United States Patent [19]

Bridges et al.

[11] Patent Number: 5,523,052
[45] Date of Patent: Jun. 4, 1996

[54] METHOD AND APPARATUS FOR RENDERING MEDICAL MATERIALS SAFE

[75] Inventors: Jack E. Bridges, Park Ridge; Guggilam C. Sresty, Burbank; Jeffrey S. Held, Chicago; James W. Sharp, Arlington Heights; Thomas J. Bajzek, Woodale, all of Ill.

[73] Assignee: Stericycle, Inc., Rolling Meadows, Ill.

[21] Appl. No.: 426,631

[22] Filed: Apr. 21, 1995

Related U.S. Application Data

[63] Continuation of Ser. No. 238,576, May 5, 1994, abandoned, which is a continuation of Ser. No. 109,403, Aug. 19, 1993, abandoned, which is a continuation of Ser. No. 972,889, Nov. 6, 1992, abandoned, which is a continuation of Ser. No. 549,588, Jul. 6, 1990, abandoned.

[51] Int. Cl.⁶ .............................. A61L 2/08; A61L 9/18; A61L 9/22
[52] U.S. Cl. .............................. 422/22; 422/26; 422/299
[58] Field of Search .............................. 422/21–22, 26, 422/299

[56] References Cited

U.S. PATENT DOCUMENTS

| | | | |
|---|---|---|---|
| 2,114,345 | 4/1938 | Hayford | 175/311 |
| 2,486,684 | 11/1949 | Schlesman et al. | 202/46 |
| 2,731,208 | 1/1956 | Dodd | 241/41 |
| 2,897,365 | 7/1959 | Dewey et al. | 422/22 |
| 2,958,570 | 11/1960 | Fessler | 422/22 |
| 3,095,359 | 6/1963 | Heller | 195/78 |
| 3,215,539 | 11/1965 | Landy | 422/22 |
| 3,261,140 | 7/1966 | Long et al. | 53/22 |
| 3,490,580 | 1/1970 | Brumfield et al. | 206/53.2 |
| 3,494,723 | 2/1970 | Gray | 21/54 |
| 3,494,724 | 2/1970 | Gray | 21/54 |
| 3,547,577 | 12/1970 | Lovercheck | 422/34 |
| 3,551,090 | 12/1970 | Brumfield et al. | |
| 3,602,712 | 8/1971 | Mann et al. | |
| 3,617,178 | 11/1971 | Clouston | |
| 3,704,089 | 11/1972 | Stehlik | |
| 3,753,651 | 8/1973 | Boucher | 422/22 |
| 3,885,915 | 5/1975 | Utsumi et al. | |
| 3,926,556 | 12/1975 | Boucher | |
| 3,940,325 | 2/1976 | Hirao | |
| 3,948,601 | 4/1976 | Fraser et al. | |
| 3,958,936 | 5/1976 | Knight | |
| 4,151,419 | 4/1979 | Morris et al. | 250/453 |
| 4,207,286 | 6/1980 | Boucher | 422/22 |
| 4,250,139 | 2/1981 | Luck et al. | 422/21 |
| 4,400,357 | 8/1983 | Hohmann | 422/299 |

(List continued on next page.)

FOREIGN PATENT DOCUMENTS

| | | |
|---|---|---|
| 1123705 | 11/1984 | U.S.S.R. |
| 1406789 | 9/1975 | United Kingdom |

OTHER PUBLICATIONS

Serota, R., "Heating with Radio Waves", Automation (Sep. 1973).

Reynolds, M., et al., "Thermoradiation Inactivation of Naturally Occurring Bacterial Spores in Soil", Applied Microbiology, vol. 28, No. 3, pp. 406–410 (Sep. 1974).

Brannen, J., "A Kinetic Model for the Biological Effects of Ionizing Radiation", Biosystems Research Department, Sandia Laboratories, SAND74–0289 (Oct. 1974). pp. 1–38.

"Progress Report: Beneficial Uses Program, Period ending Dec. 31, 1976", Waste Management and Environmental Programs Department, Sandia laboratories, SAND77–0426 (1977). pp. 5–7, 9–44.

(List continued on next page.)

*Primary Examiner*—Lyle A. Alexander
*Attorney, Agent, or Firm*—Fitch, Even, Tabin & Flannery

[57] ABSTRACT

Infectious medical materials are rendered harmless by heating heterogeneous medical materials having wet and dry portions with a radio-frequency electric field. The medical materials are exposed to the radio-frequency electric field in order to heat the medical materials to inactivate microorganisms thereon. The medical materials are then irradiated with gamma radiation to inactivate microorganisms remaining viable thereon after application of the radio-frequency electric field.

19 Claims, 15 Drawing Sheets

U.S. PATENT DOCUMENTS

| | | | |
|---|---|---|---|
| 4,457,221 | 7/1984 | Geren | 99/451 |
| 4,524,079 | 6/1985 | Hofmann | 422/22 |
| 4,552,720 | 11/1985 | Baker et al. | 422/26 |
| 4,599,216 | 7/1986 | Rohrer et al. | 422/21 |
| 4,620,908 | 11/1986 | Van Duzer | 422/22 |
| 4,652,763 | 3/1987 | Nablo | 250/492.3 |
| 4,671,935 | 6/1987 | Rohrer et al. | 422/22 |
| 4,746,968 | 5/1988 | Wear et al. | 219/10.55 |
| 4,775,770 | 10/1988 | Fritz | 219/10.55 |
| 4,801,427 | 1/1989 | Jacob | 422/23 |
| 4,808,782 | 2/1989 | Nakagawa et al. | 219/10.55 M |
| 4,808,783 | 2/1989 | Stenström | 219/10.55 M |
| 4,818,488 | 4/1989 | Jacob | 422/22 |
| 4,896,010 | 1/1990 | O'Connor et al. | 422/21 |
| 4,917,586 | 4/1990 | Jacob | 422/21 |
| 4,931,261 | 6/1990 | Jacob | 422/21 |
| 4,943,417 | 7/1990 | Jacob | 422/21 |
| 4,978,501 | 12/1990 | Diprose et al. | 422/22 |
| 5,019,344 | 5/1991 | Kutner | 422/21 |

OTHER PUBLICATIONS

Chipley, J., "Effects of Microwave Irradiation on Microorganisms", Advances in Applied Microbiology, vol. 26, pp. 129–145 (1980).

Sivinksi, J., "General Description of the Sludge Irradiation Process", National Symposium on the Use of Cesium–137 to Process Sludge for Further Reduction of Pathogens, SAND80-2744 (Dec. 1980). pp. 57–68.

Tonetti, R., "Disease Control Requirements for Various Sludge Uses", National Symposium on the Use of Cesium–137 to Process Sludge for Further Reduction of Pathogens, SAND80-2744 (Dec. 1980). pp. 43–56.

"Dielectric Heating: RF and Microwave", EPRI Center for Materials Fabrication, Tech Commentary, vol. 4, No. 1 (1987). pp. 1–4.

"Gamma Processing Equipment", AECL Industrial Radiochemical Co., Irradiation Division product brochure (Jan. 1987). pp. 1–15 & photographs.

Paul, B., "Combustion Says Firm Sterilizes Medical Waste With Microwaves", Wall Street Journal, Apr. 10, 1989, p. B3.

"A Microwave Sterilizer is Developed", New York Times, Science Watch, Jun. 20, 1989.

Hall, Steven K., "Infectious Waste Management: A Multifaceted Problem," Pollution Engineering, 74–78 (Aug. 1989).

"Medical Waste Treatment by Microwave Technology", product brochure, Norcal Solid Waste Systems, publication date unknown.

"Dielectric Heating", product brochure, PSC, Inc., publication date unknown.

Ward, J., "Molecular Mechanisms of Radiation-Induced Damage to Nucleic Acids", unknown source and publication date. pp. 183–231.

"Electromagnetic Radiation and Ionizing Energy", unknown source and publication date. pp. 6–8, 32–33, 35–50.

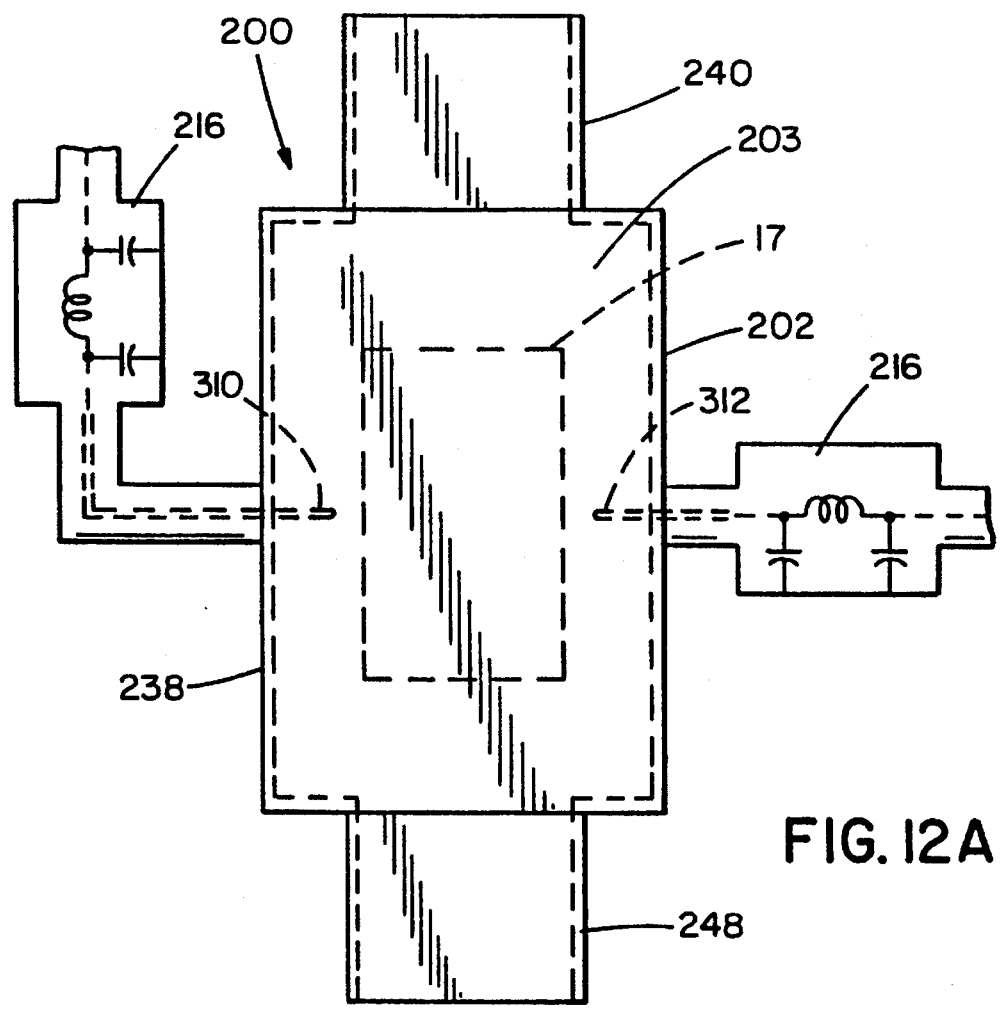
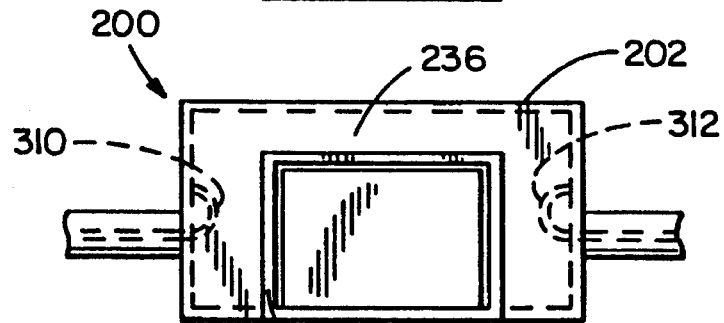
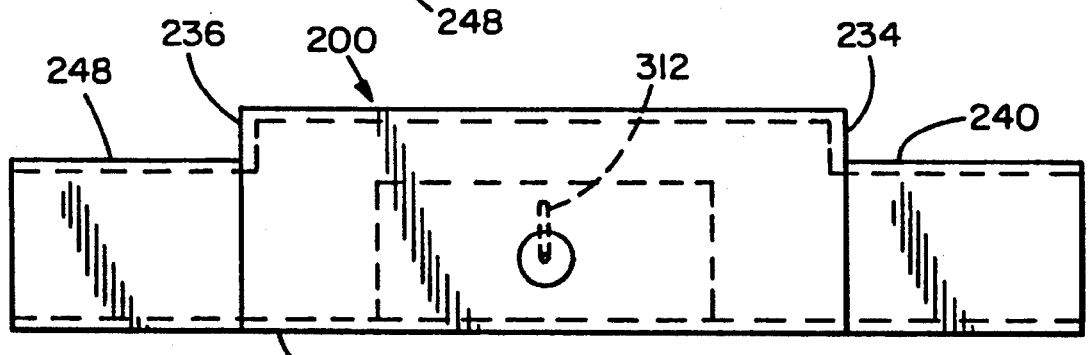
FIG. 12A
FIG. 12B
FIG. 12C (a) TE$_{10}$ MODE POWER DENSITY (b) TE$_{20}$ MODE POWER DENSITY (c) 0.864 TE$_{10}$ + 0.48 TE$_{20}$ POWER DENSITY

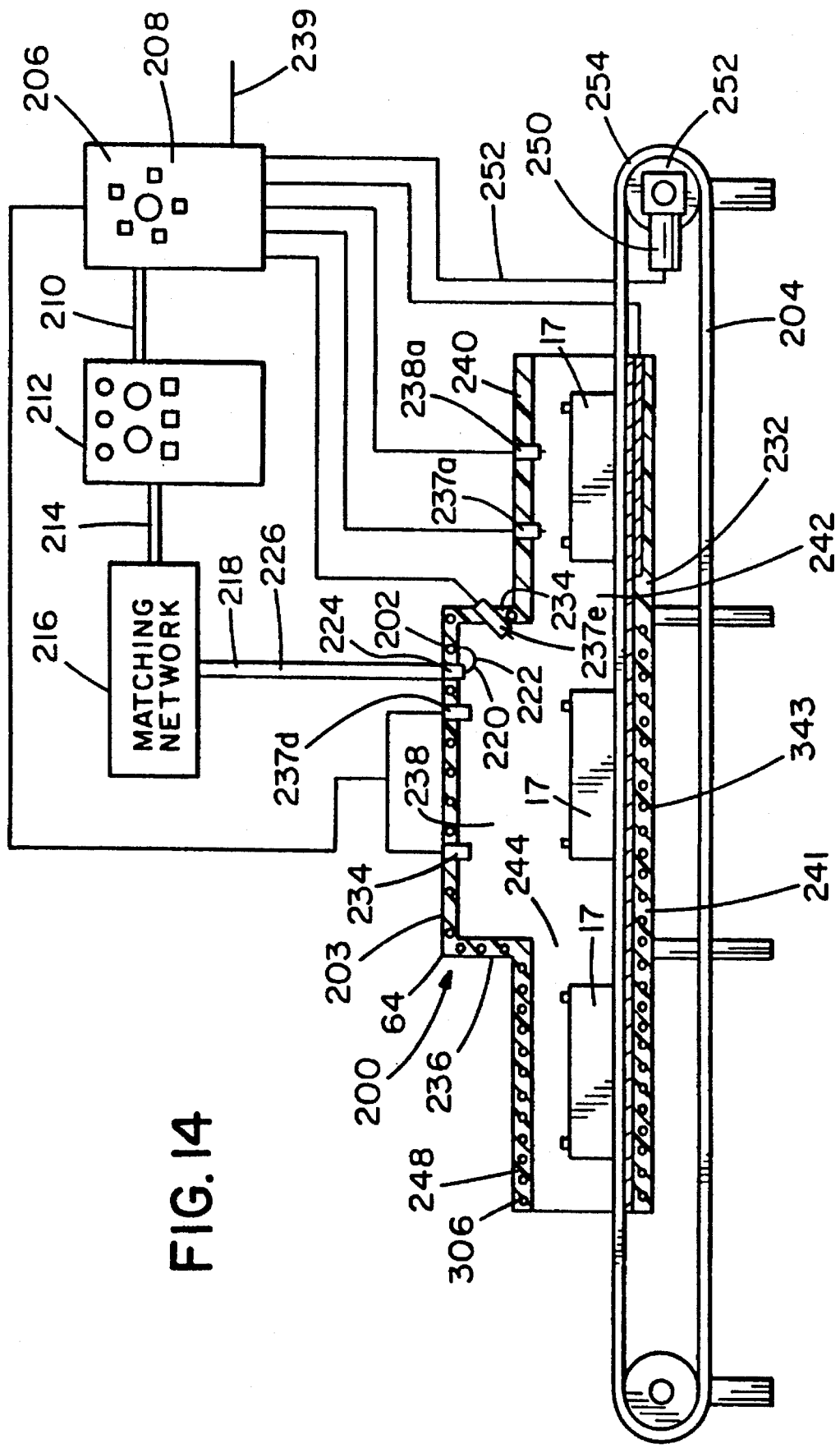

METHOD AND APPARATUS FOR RENDERING MEDICAL MATERIALS SAFE

This application is a continuation of application Ser. No. 238,576 filed May 5, 1994, now abandoned, which application is a continuation of application Ser. No. 109,403 filed Aug. 19, 1993, now abandoned, which application is a continuation of application Ser. No. 07/972,889 filed Nov. 6, 1992 now abandoned, which application is a continuation of application Ser. No. 07/549,588 filed Jul. 6, 1990, now abandoned.

BACKGROUND OF THE INVENTION

The present invention relates generally to a method of disinfecting medical materials and more particularly to a method and apparatus for disinfecting medical materials by exposing the materials to radio-frequency waves and ionizing radiation. The term medical materials encompasses medical waste, veterinary waste, and medical products.

The problems with current medical waste handling methods, like the problems of solid waste disposal in general, are becoming increasingly acute. Solid waste is primarily disposed of by burning or by burial in landfill. Both of the methods have severe disadvantages. Burning of solid waste liberates waste particles and fumes which contribute to acid rain and other pollution of the atmosphere. Burying the waste results in possible leaks of toxic chemicals into the surrounding earth and contamination of ground water supplies. Although increasing amounts of solid waste are being recycled, which alleviates the problems of incineration and burial, presently available recycling methods do not provide a complete solution to the disposal problem.

Waste disposal is of even more urgent concern when the waste comprises possibly infectious medical waste. Such infectious medical waste is a by-product of veterinary and medical care. For example, regulated medical waste consists of: (1) cultures and stocks of infectious agents and associated biological materials; (2) pathological wastes; (3) human blood and blood products; (4) contaminated sharps, including needles, syringes, blades, scalpels, and broken glass; (5) animal waste; (6) isolation waste, including gloves and other disposable products used in the care of patients with serious infections; and (7) unused sharps. These wastes can generally be divided between (a) general medical waste, including cultures and stocks of infectious agents, associated biologicals, pathological waste, and human blood and blood products; (b) veterinary waste, including animal waste; and (c) waste that is predominately plastic, such as the contaminated and unused sharps and isolation waste. The predominately plastic waste also includes metal as well. Hospitals typically segregate waste by types. Contaminated sharps and isolation waste, however, are of special concern as they may carry highly dangerous pathogens such as AIDS virus or hepatitis virus. Sharps in particular have caused widespread public concern when observed washed up on beaches or in public areas.

Hospitals and other generators of medical and veterinary waste employ three methods of waste handling: (a) on-site incineration of the waste, (b) on-site steam autoclaving of the waste followed by later shipment to a landfill for burying, and (c) collection of the waste by a licensed waste hauler with no on-site processing.

Many hospital incinerators, even those located predominately in urban areas, emit pollutants at a relatively high rate. The Environmental Protection Agency has identified harmful substances in the emissions of such hospital incinerators. They include metals such as arsenic, cadmium and lead, organic compounds, such as ethylene, dioxins and furans, acid gases and carbon monoxide as well as soot, viruses and pathogens. Emissions from these incinerators may be a more significant public health hazard than improper dumping [Steven K. Hall, "Infectious Waste Management: A Multifaceted Problem," Pollution Engineering, 74–78 (Aug. 1989)].

Although steam autoclaving may be used to sterilize waste before further processing, it is expensive and time consuming. Heat denatures the proteins and microorganisms causing protein inactivation and cell death in a short time. Temperature monitoring devices such as thermocouples, and biological indicators, such as heat resistant *Bacillus stearothermophilus* spores, may be used to assure effective sterilization.

U.S. Pat. No. 2,731,208 to Dodd teaches a steam sterilizing apparatus for disposing of contaminated waste which incorporates shredding the waste ("including paper containers such as used sputum cups," col. 1 lines 287–29). Dodd teaches blowing steam into a container full of waste and processing only limited types of items. The Dodd system has the disadvantage of depositing the shredded final mixture into a sewer, which would cause further environmental problems.

Whether or not the hospital first autoclaves its medical wastes, including broken needles and glass, the waste is then turned over to a licensed waste hauler for transport to a landfill or other depository. U.S. Pat. No. 3,958,936 to Knight discloses compaction of hospital waste for more efficient landfill disposal. Specifically, the reference teaches the application of heat in the range of about 204° C. to 316° C. to hospital and other waste to melt the plastic and convert it into a hard compact block for safer disposal in landfills. The waste is disinfected by the high temperatures, and sharps, such as needles, become embedded in the plastic where they are a reduced mechanical hazard. However, this method suffers from the disadvantage of requiring relatively high temperatures necessitating large energy expenditures and landfill disposal. Metropolitan landfills are becoming filled, and unauthorized dumping is a problem.

A further area of concern is the sterilization of medical products prior to use. By medical product is meant any product which must be sterilized prior to use in health care. This is exemplified but not limited to needles, syringes, sutures, bandages, scalpels, gloves, drapes, and other disposal items. Many reusable items also must be provided in sterile form. Widespread current sterilization methods include the use of autoclaving, ethylene oxide, and ionizing radiation such as gamma radiation. The heat and humidity of autoclaving are quite damaging to many disposable metal products. Ethylene oxide and ionizing radiation are preferred commercially in those cases.

In order to sterilize medical products, poisonous ethylene oxide gas may be used in a closed chamber containing the products to be sterilized. For effective sterilization, not only must the ethylene oxide concentration be controlled carefully, but the temperature, humidity, and porosity of the sterilizer load also must be carefully regulated. Ethylene oxide is relatively slow to dissipate from plastics and its use may require that medical products be stored until the ethylene oxide concentration decreases to a safe level. Ethylene oxide also must be carefully vented to the atmosphere subsequent to the sterilization cycle in order to avoid poisoning operators of the sterilization apparatus.

Ionizing radiation, such as gamma radiation, may be used to sterilize medical products within their packaging; however, it must be administered at such high doses that many plastics become yellow and brittle due to the gamma rays having altered the structure of the polymers of which they are made. For example, U.S. Pat. No. 3,940,325 to Hirao teaches methods for adjusting the formulas of plastics for medical syringes to avoid yellowing and cracking due to exposure to sterilizing gamma radiation. Other substances may also be damaged by exposure to gamma radiation. Such ionizing radiation sterilizes because its high energy photons damage and thereby inactivate the DNA of organisms such as bacteria and viruses. As a result of the inactivation of the DNA, cells lose their ability to reproduce and thereby cause infections. On a large scale industrial basis, ionizing radiation, especially gamma radiation from cobalt 60, has been used to sterilize medical products prior to their use in patients. However, the radiation levels necessary to sterilize may also damage the product being sterilized.

Other methods have been suggested for sterilization of medical products. For instance, U.S. Pat. No. 3,617,178 to Clouston teaches a method of improving sterilization efficiency by increasing hydrostatic pressure. Elevated hydrostatic pressure causes sterilization resistant bacterial spores to germinate, or begin to grow. However, it has no effect on viruses. Bacterial germination, which converts the bacteria from their environmentally resistant spore form, makes the bacteria more sensitive to radiation, so that lower doses may be employed. Clouston further teaches optimizing the hydrostatic pressure effect by adjusting the temperature up to 80° C. According to Clouston, elevated pressure in heated fluid or moist gas is essential to the method. Elevated temperature alone has a negligible effect. Furthermore, the pressure, heat, or moisture treatment taught by Clouston is intended to cause bacterial spores to germinate thereby rendering them more vulnerable to sterilization techniques, not to sterilize or inactivate microorganisms.

In contrast, U.S. Pat. Nos. 4,620,908 to Van Duzer and 3,704,089 to Stehlik teach prefreezing injectable proteins and surgical adhesive prior to irradiation with gamma radiation from cobalt 60 for aseptic manufacture of those materials. U.S. Pat. No. 3,602,712 to Mann discloses an apparatus for gamma irradiation and sterilization of sewage and industrial waste.

Besides gamma radiation, other types of electromagnetic radiation have been considered as potential sterilants in known systems. Microwaves are increasingly being investigated for rapid sterilization of individual medical devices as well as shredded medical waste. Recently, an experiment showed that metallic instruments could be sterilized in only 30 seconds in a microwave oven (*New York. Times*, "Science Watch Microwave Sterilizer is Developed," Jun. 20, 1989). That particular method, however, suffers from the drawback that only a few such metallic instruments can be treated at a particular time. It is not particularly applicable for treatment of medical waste in bulk, and in particular for treatment of medical waste which has been bagged.

United Kingdom Patent No. 1 406 789 to Boucher discloses a microwave system for the surface sterilization of reusable laboratory, medical, and dental instruments in a moist atmosphere at a lower temperature than those presently used and in a shorter time. The system is intended to render aseptic reusable instruments for medical use and generates electromagnetic energy having frequencies between 100 megahertz and 23000 megahertz. Boucher emphasizes that "his invention deals exclusively with surface sterilization" and that he "does not intend to cover such special cases" as "'in-depth' sterilization" (page 1, lines 58–67). Boucher teaches that only through a combination of proper humidification with the thermal and nonthermal effects of microwave radiation can reproducible and satisfactory results be obtained with a wide variety of species, including thermoresistant spores" (page 1, lines 77–83). Boucher teaches the placement of the object to be sterilized in a gas-tight container with a source of water vapor.

Soviet Union Patent No. 1,123,705 also discloses a method of sterilizing medical instruments for reuse by UHF treatment. For injection needles it discloses a final temperature of 160° C. to 470° C. and for acupuncture needles it discloses a final temperature of 160° C. to 270° C.

Systems are also known for treatment of disposable medical waste utilizing microwaves. This system first shreds the waste, sprays the shredded waste with water, and passes the wet shredded waste through a microwave chamber designed to raise the temperature of the wet shredded waste to 205° C. to disinfect it. After the disinfection step, the system compresses the disinfected shredded waste and packages it for shipment to landfills or incinerators (*The Wall Street Journal*, p. B-3, Apr. 10, 1989). One potential problem with this system is that shredding before sterilization could release infectious particles to the environment and may thus spread contagion. Another problem is the ultimate disposal of the waste; it persists in landfills or may pollute the air when incinerated.

Also of interest is a method and apparatus for using microwave frequency electromagnetic fields to heat medical waste to disinfect it. "Medical Waste Treatment By Microwave Technology", Norcal Solid Waste Systems. The system includes equipment for receiving the medical waste, shredding it into particle sizes of 1 to 1½ inch linear dimension, and applying steam to the shredded waste to increase its moisture content, as well as to inactivate certain of the microorganisms thereon. The waste is then carried to a microwave treatment area where microwave energy heats the waste to 203° C. for a selected amount of time. A holding area may provide heat sealing. The waste is then recirculated to the steaming station where steam is again applied to inactivate further microorganisms which may still be active in the waste which is shredded and disinfected, disposed in a dumpster for placement in a landfill. It may be appreciated, however, that volumetric heating cannot take place in such a microwave system that the waste has to be scattered in a relatively thin layer on a conveyor belt for treatment by the microwave radiation as the microwave radiation does not adequately penetrate the material. In addition, the material is not enclosed so that there is no substantial transfer of moisture from wet materials to dry materials to aid in the heating within the enclosed system.

U.S. Pat. No. 3,547,577 to Lovercheck discloses a machine for treating garbage by shredding, compressing the shredded garbage into briquettes, and sterilizing the briquettes with gas. After shredding the garbage is separated into magnetic and nonmagnetic portions. The sterilization step employs ethylene oxide gas which requires temperature control. The briquettes are maintained at a temperature of about 54° C.

Further, microwaves are limited in their penetration and are ineffective for heating when applied to large scale, boxed medical waste of the type which comprises the waste disposal problem today. Microwaves do not heat very effectively because they do not penetrate very deeply. Most of the heat is generated near the surface and quickly dissipates into the surroundings, in part because it is not well conducted into the center portions of the boxed medical waste. In contrast, radio-frequency waves at relatively low frequency can penetrate boxed medical waste more deeply.

It also is known in the art that thermal radiation treatment of bacterial spores and other pathogens may allow greatly reduced ionizing radiation dosage to accomplish sterilization of a given population. For instance, in "Thermoradiation Inactivation Of Naturally Occurring Bacterial Spores In Soil," M. C. Reynolds et al., *Applied Microbiology*, Vol.28, No. 3, September 1974, it is disclosed that bacterial spores may be inactivated by heating them with dry heat and exposing them to ionizing radiation from a cobalt 60 source allow greatly reduced treatment times over the use of either dry heat or radiation alone.

An attempt to elucidate a model for such behavior is set forth in J. P. Brannen, "A Kinetic Model For The Biological Effects Of Ionizing Radiation", Sandia Laboratories, SAND74-0289(October 1974).

Heat and radiation inactivation of bacteria are discussed at "Progress Report Beneficial Uses Program, Period Ending Dec. 31, 1976", Waste Management and Environmental Programs Department, Sandia Laboratories, SAND77-0426 (1977), where it is taught that viruses in sewage sludge may be destroyed by evaporation. Heat inactivation may be used to destroy *Salmonella enterititis* ser. *montevideo*. Streptococcus bacteria may be destroyed by using ionizing radiation at a dose of about 140 kilorads.

The use of cesium 137 to inactivate pathogens in sludge is discussed in "Sludge Or Radiation Disinfection For Beneficial Use", Applied Biology And Isotope Utilization Division 4535, "General Description Of The Sludge And Radiation Process", SAND80-2744 (December 1980), where it is disclosed that cesium-137, emitting gamma radiation may be used to inactivate pathogens in sewage sludge See also, "Use Of Cesium-137 To Process Sludge For Further Reduction Of Pathogens, Sludge Or Radiation Disinfection For Beneficial Use," Disease Control Requirements For Various Sludge Uses, Applied Biology and Isotope Utilization Division 4535, SAND80-2744 (December 1980), which discloses that in order to render sewage sludge safe, in particular for certain agricultural usages, irradiation may be used as an add-on process in conjunction with sterilization where sludge is maintained at 30 min. at a temperature of at least 70° C. In each of the aforementioned papers, it may be appreciated that the sludge which is being treated is substantially homogeneous in its dielectric characteristics and, thus, in its heating characteristics.

The gamma irradiation equipment commonly used and disclosed in this application is of the type disclosed in "Gamma Processing Equipment", AECL Industrial and Radiation Division (January 1987).

The dual plate 12 megahertz plate type radio-frequency heater is of the type disclosed in "Dielectric Heating" PSC Inc which although undated, constitutes prior art to this application.

Like microwaves, radio-frequency waves are a form of electromagnetic energy. They also transfer energy directly into materials, primarily by the interaction of their time-varying electric fields with molecules. Radio-frequency waves may be applied by connecting a radio-frequency alternating current to a pair of electrodes. Between the two electrodes an alternating radio-frequency electromagnetic field having a time-varying electric field component is established. When objects are placed between the electrodes in the time-varying electric field, the time-varying electric field partially or completely penetrates the object and heats it.

Heat is produced when the time-varying electric field accelerates ions and electrons which collide with molecules. Heat also is produced because the time-varying electric field cause molecules, and particularly those with a relatively high electric dipole moment, to rotate back and forth as a result of the torque placed upon them by the time-varying electric field. Most large molecules, or molecules with evenly distributed charge, have relatively low or nonexistent dipole moments and are not very much affected by the radio-frequency time-varying electric field. Small molecules, in particular with polar groups, have relatively large electric dipole moments and thus have relatively large torques exerted upon them by the time-varying electric field. In particular, highly polar molecules, like water, experience relatively large torques and as a result are rotated by the time-varying electric field, thereby transferring mechanical energy to their surroundings as internal energy or heat. Lower frequency time-varying electric fields penetrate deeply and heat objects more evenly. Relatively high frequency time-varying electric fields do not penetrate as deeply, but heat more rapidly the portions of objects they interact with.

It should be noted that a time-varying electric field is always accompanied by a time-varying magnetic field, except where destructive cancellation occurs with interference patterns. For most materials being considered here, the principal heating mechanism arises from the electric fields. These fields can cause both ohmic heating via induced ionic currents and dielectric heating via molecular stressing from the internal electric fields. For very moist materials, the presence of the accompanying time-varying magnetic field can also induce eddy-currents which can also heat the material. Also, some type of combined effect of magnetic fields and heat may occur. While the ensuing discussion is presented in context of an electric field effect, it should be understood that the effects of accompanying time-varying magnetic field are defined here for simplification as part of the electric field phenomena.

Because different materials are composed of different types of molecules with differing electric dipoles, they heat at different rates when exposed to a given time-varying electric field. For example, plastics, which are formed of very large polymer molecules, are not heated by time-varying electric fields as rapidly as water. Metal objects may or may not be easily heated when exposed to time varying electric fields either in the radio-frequency or microwave region. The high conductivity of the metal objects tends to short out the electric fields and rescatter them. As a consequence, there are many conditions where metal objects are difficult to heat, as exemplified by the metal liner of the interior microwave ovens. On the other hand, such time-varying fields can also induce substantial currents which flow on the outside of the metal objects. Under certain circumstances heating effects will occur on the surface of the metal object which, in the case of a small needle, the heat is readily diffused into the interior. In addition, the presence of long, thin metal objects in an electric field causes enhancement of the electric field intensity near the ends of the metal objects and a diminution or shadowing of the fields near the middle. Thus, if the electric field is parallel to the axis of the metal object, strong electric fields will exist near the tips and weak electric fields will exist near the center of the rod or needle. Such field enhancements can lead to arcing and possible fires. In addition, the field suppression or shadowing of such metal objects is also an unwanted feature if the presence of a single electric field vector is-relied upon in its entirety to provide the sterilization. The failure of the radio-frequency electromagnetic field to penetrate the object causing surface heating only, or the opposite failure of the materials to absorb the electric field energy, causes uneven heating of the medical waste. The uneven heating is exacerbated because the medical waste usually comprises mixed materials which are difficult to heat effectively using radio-frequency energy due to the presence of areas of high field absorption, such as are due to metals and concomitant shadowing and cold spots. In addition, similar but less pronounced absorption effects are found with water molecules. Thus, when heterogeneous or mixed medical wastes have wet and dry portions, it may be seen that only the wet portions of such material would be heated. Mixed loads such as hospital wastes were considered impossible to sterilize by radio-frequency energy because the waste contains a wide variety of materials, each having different dielectric properties. A great concern was that the presence of a sufficient number of metallic sharps would lead to arcing, causing ignition of the accompanying dry wastes. Another concern was that even if fire was not started, the differential energy absorption of fluids and sharps would leave dry objects unsterilized.

In fact, other attempts to kill microorganisms with radio-frequency energy have been considered unsuccessful In his 1980 review, "Effects Of Microwave Irradiation On Microorganisms", *Advances in Applied Microbiology* 26:129–45, Chipley cites an experiment of applying radio-frequency energy to bacteria and viruses which grow on tobacco. The experiment found no effect of the radio-frequency energy on the bacteria and viruses. In another study of radio-frequency energy on contaminated liquid food, there was no showing of "selective killing effect" except when ethanol was added.

In the same review, Chipley cited numerous tests of microwaves on microorganisms and concluded that "results of tests for viability of *B. subtilis* spores also showed identical death curves compared with those obtained by conventional heat." On the other hand, however, Chipley cites several references which support the view that microwave irradiation has collateral thermal and nonthermal effects. [For example, Culkin and Fung (1975) found that microbial destruction occurred at reduced temperatures and shorter time periods when the material was exposed to microwaves as compared to conventional heating methods. Wayland et al., 1977 also demonstrated the interdependence of heat and microwaves effects in the studies of spores of *B. subtilis*.

U.S. Pat. No. 2,114,345 to Hayford discloses a radio-frequency applicator with electroscopic control for destroying bacteria in bottled beer and similar products. Hayford teaches an apparatus for sterilizing a series of small objects. The radio-frequency field must be constantly readjusted by the electroscopic control. There is no teaching or suggestion that large scale sterilization of heterogeneous waste could be carried out.

U.S. Pat. No. 3,948,601 to Fraser et al. teaches the indirect use of radio-frequency energy in sterilizing medical and hospital equipment as well as human waste. The reference teaches the use of radio-frequency energy for heating gases, particularly argon, and exciting them so that they ionize into a plasma having a temperature of approximately 100° C. to 500° C. The reference teaches that a cool plasma at a temperature of only 25° C. to 50° C. and very low pressure may effectively sterilize an article. However, sterilization by plasma does not suggest the direct use of radio-frequency waves in sterilization since it is the chemical reactive effect of the plasma which presumably performs the sterilization function rather than the direct or thermal effects of radio-frequency energy on pathogens contained on the material. It may be appreciated that only those portions of the equipment and waste actually contacted by the plasma would be treated.

Reprocessing of the waste, and especially medical waste, is also vital for several reasons. Even if the medical waste has been rendered harmless or innocuous by the destruction of any pathogens associated therewith, there is still the problem of the disposal of the bulk material including the plastics, the sharps, and fibrous material such as gowns, diapers, and the like. The material is relatively bulky and landfills, particularly in many urban areas, have become filled. In addition, older landfills may leak and nonpathogenic but chemically polluting substances may leak into surrounding ground water, causing health hazards. Thus, burying the sterilized medical waste is becoming less attractive. Further, merely burning the sterilized medical waste can pollute the atmosphere and cause acid rain. Current reprocessing technology should be employed to process the sterilized medical waste for effective utilization and proper disposal. What is needed is a method for sterilizing the medical waste and destroying the pathogens thereon and disposing of the sterilized waste in a manner which is harmless to health care workers, waste handlers, and the public at large.

A series of investigations has been undertaken as to sterilization, especially for food. This has resulted in patents or inventions wherein the material to be treated is housed in a microwave transparent container such that the material can be heated at vapor pressures which coexist with temperatures of 120° C. These include Gray U.S. Pat. No. 3,494,723; Nakagawa U.S. Pat. No. 4,808,782; Stenstron U.S. Pat. No. 4,808,783; Landy U.S. Pat. No. 3,215,539; Utosomi U.S. Pat. No. 3,885,915; and Fritz U.S. Pat. No. 4,775,770. All of these patents disclose heating homogeneous material in some form of pouch or pressure container where the material, typically food, is homogeneous. They do not address the special problem considered here where the material is heterogeneous and contains sharps, moist materials and dry materials.

SUMMARY OF THE INVENTION

The present invention provides a method and apparatus for processing medical materials such as medical and veterinary waste and medical products which disinfects the materials by heating them with radio-frequency energy and irradiating them with gamma radiation from cobalt 60. That is, it achieves at least a ten-fold reduction in the population of *Bacillus stearothermophilus* var. *niger*. The invention disinfects bulk medical waste by heating it with a radio-frequency electric field to inactivate viruses and thereon and irradiating with gamma radiation to inactivate bacteria thereon. The purpose of radio-frequency heating prior to the ionizing radiation step is to reduce the radiation dose needed to achieve disinfection. Since the cost of irradiating is high, the overall economics are improved. It has been found that by heating the waste to over 60° C. the gamma radiation for disinfection can be reduced by a factor of three. The medical waste is heterogeneous, that is, it comprises wet and dry materials such as dressings, diapers, tissue and the like and material such as plastic gloves, plastic syringes and the like. The medical waste also contains metal containing sharps as such hypodermic needles, suturing needles, scalpels and the like. The waste is exposed to a radio-frequency electric field having a frequency of in the range of 500 kilohertz to 600 megahertz, preferably about from 10 megahertz to about 100 megahertz. The lower frequencies of operation are preferred to assure good depth of penetration of the electric fields into the more moist material. If microwave frequencies are used (above 900 MHz), the depth of penetration is often less than a few centimeters. The depth of penetration is decreased by increasing the moisture content.

While not wishing to be bound by any particular theory, it is noted that the time-varying electric field heats the water on the wet portions and boils off a portion of it. The evaporated water or water vapor apparently travels by convection and diffusion throughout the bag containing the medical waste and may condense on the cooler, dry portions because, other than the metal-containing sharps, dry material has not been heated substantially by the time-varying electric field. It is believed that the condensation of moisture on the formerly dry material gives up heat of vaporization and thereby transfers heat to the previously dry material. It is believed that this transfer of moisture also makes the materials relatively homogeneous with respect to water content. This permits all of the material to be rapidly heated volumetrically by the field. The condensed moisture on or in the previously dry material can now absorb energy from the electric field. This generates heat within or on the previously dry material which is now rapidly heated by the field.

One step of the pressure-vessel method comprises shredding or comminuting the medical waste into materials of about 1 to 2 inches linear dimension. The comminuted waste optionally has water added in the form of a spray or an aqueous foam to aid in the absorption of radio-frequency energy and conversion into heat. The comminuted medical waste is then housed within a closed fire-resistant epoxy-fiberglass container and the radio-frequency electric field is applied to raise the internal temperature of the container to about 60° C.

The vapor-containing version of this invention is suitable to treat a wide variety of wet and dry conglomerations of permeable material which must be raised to temperatures below or close to that of the vaporization point of water. The use of radio-frequency heating in such a container creates volumetric heating and reduces the time requirements associated with autoclaving. The invention also is useful for the treatment of certain nonuniform moisture content commodities which are highly permeable, such as breakfast cereals, tobacco, and whole grains, which are highly permeable to gas flow while at the same time often require heating treatments to disinfect the produce, to kill insect infestations and to equalize the moisture contents.

In another embodiment, to implement the vapor-containing version of the process, the materials to be treated may be collected and eventually placed in a container capable of withstanding temperatures, for about 15 minutes, of just above the vaporization point of water which, in this case for sea-level atmospheric pressure, would be just above 100° C.

Thus, by selecting this type of specific packaging, several of the requirements for the successful vapor-containment, radio-frequency preheating step of the disinfection process are realized. First of all, a vapor impermeable barrier is placed around the medical material. Secondly, the heat capacity of the vapor barrier is small since the wall thickness of the plastic material is usually about one quarter inch. Thirdly, thermal transfer outside the treatment material is inhibited by the thermal insulating properties of the epoxy-fiberglass container.

One of the embodiments of the invention additionally comprises the step of transferring heated medical waste to a heat-soaking area which maintains the elevated temperature for about 45 minutes. The temperature is maintained in an energy effective and cost efficient fashion in order to provide extra assurance that all pathogens are destroyed by the heat.

In some versions, the walls of the cavity or belt are heated to a temperature that is comparable to the temperature of the material being processed. As a consequence, in the case of the invention at hand, little or no energy is transferred out of the items to be heated. The purpose of minimizing this transfer is that if the surface is too hot, the material becomes sticky and gummy and thereby eventually clogs the mechanics of the system. On the other hand, if the wall material is significantly lower than that of the material being processed, energy is lost from the material being processed. In the case of wet or moist material where a high energy absorption occurs, this may not be a significant problem, but it can be significant in the case of very dry materials. These have little dielectric absorbing ability and therefore have little capability to simultaneously heat themselves and the adjacent walls. To overcome this, a preferred embodiment of the invention employs the use of peripheral guard heaters along the walls such that the wall temperature assumes approximately the same temperature as that of the material being processed. Alternatively, insulated wall materials may be used which have low thermal conductivity and heat capacity, whereby the heated gases from the material being processed can easily heat the wall so that they can be heated such that the wall temperature can immediately rise to the temperature of the material being processed. The medical material can be exposed in a container to the radio-frequency energy such that the temperature of the material or medical waste is first heated to about 60° C.

The tumbling process also ensures exposure of all the material to the electric fields to take advantage of collateral thermal and nonthermal effects which may exist at about 90 and may allow complete sterilization to be accomplished without a significant degree of vaporization.

Another embodiment of the invention also comprises steps of further processing the medical waste by presorting the material into recyclable plastic or refuse derived fuel, comminuting or shredding both types of materials, repackaging and shipping to commercial users.

In a still further embodiment of the invention, the medical material, specifically comprising medical and veterinary waste, is received for processing. The waste is then comminuted or shredded to an average linear particle dimension of 1 to 2 inches. If the waste is particularly dry when it is packed in a container for processing, water or foam may be added to the waste. The foam specifically comprises a surfactant such as a detergent mixed with water. The shredding reduces the particle size and reduces the field intensities in any metal materials in the particles in order to reduce the likelihood or intensity of arcing when the shredded material is exposed to the radio-frequency radiation. The container also may be lined with wetted material such as wetted cardboard to increase its RF absorption.

In most cases, water need not be added to the material as the material contains up to ten per cent water by weight. Thus, when the material is heated by the radio-frequency field, water from the wet material is vaporized, transported to the dry material where it condenses, and couples with the radio-frequency radiation to heat the dry material. In the event that water is to be added, it may be added to the container in several ways. First, it may be sprayed on in the form of a misting stream or may be simply be used to soak the shredded material. If large amounts of water, however, are used, the radio-frequency energy may be substantially reflected away from the interior of the container causing the processing time to increase or requiring that higher power equipment be used to obtain reasonable heating times. In order to reduce the amount of reflection, the water may be added in the form of foam which is volume filling, but which has a relatively low average dielectric constant. In experiments which we have performed, foam having a dielectric constant of about 1 to about 10, rather than 80, has been employed, causing only about 10% of the input power at 12 megahertz to be reflected, rather than about 90% of the input power, as happens with volumes of liquid water. The foam also provides a quenching medium for reducing the likelihood of fires within the container. The container is an epoxy fiberglass container which is sealed.

Before the medical materials are heated, they may also be compacted to allow more material to be heated at any one time and to cause the dielectric material, including the foam and insulating material in the medical waste, to be driven into more intimate contact with any metal therein, causing a reduction in the likelihood of arcing and fires in the medical material when it is heated. Reduction in fires is also achieved in this alternative method by the use of the sealed containers composed of the fire-resistant plastic, which limits the amount of oxygen within the container, to prevent fires from spreading if arcing causes partial combustion of the contents.

In a preferred embodiment of this alternative, steam generated by evaporation of the moisture present in the medical materials is used to generate or to maintain the pressure inside the radio-frequency treatment chamber. The walls and other interior parts of the radio-frequency treatment chamber are maintained at or slightly above the required treatment temperature in order to minimize heat losses and steam condensation. It is also preferred to minimize the volume of free air space inside the radio-frequency treatment chamber to reduce the total volume of oxygen available to cause combustion, and to reduce the volume of steam required to pressurize the radio-frequency treatment chamber. The radio-frequency treatment chamber may be provided with an adjustable pressure relief valve. The pressure setting can be increased, if required, to, increase the temperature of treatment.

Once the material has been heated to 60°–70° C. and partial disinfection has taken place by inactivating the viruses on the materials, further disinfection is carried out by exposing or irradiating the medical waste whether in comminuted or whole form to gamma radiation emitted by a cobalt 60 source. In the preferred embodiment, a commercial irradiation unit of the type available from AECL having approximately one million curies of cobalt 60 source is used for irradiating the medical material on which the bacteria and bacterial spores are to be destroyed. In the previous types of gamma ray sterilization systems 1.5 megarads or more were required in order to insure that the material was adequately disinfected. The prior step of heating in combination with the gamma radiation allows only 0.5 megarads to be used for the disinfection rather than the 1.5 megarads. As the throughput rate through the gamma ray irradiator is primarily dependent upon the amount of or dosage of radiation which a particular sample to be disinfected is to receive the lower the radiation required the more rapidly a known quantity of material can be processed and thus, more material can be disinfected in a gamma ray facility having a selected source strength.

In order to further enhance the process of gamma ray disinfection, we have found that following the comminution step and in some cases, even without the comminution step recited above, the medical or hospital waste, which usually has a density of five to ten pounds per cubic foot, may be compressed up to densities of 28 pounds per cubic foot, with no increase in the amount of time which the material need be exposed to the gamma ray source within the gamma ray irradiator. Thus, the mass throughput of hospital waste through the gamma ray irradiator can be drastically increased by the step of compacting the material prior to exposure to the gamma ray source.

It is believed that the gamma ray source destroys or inactivates the bacteria and certain of the bacterial spores on the medical materials or medical waste to be disinfected by dimerizing the deoxyribonucleic acid on and in the bacteria and bacterial spores which are found and which contaminate the medical materials.

Therefore, in view of the foregoing, it is a primary object of the present invention to render harmless or disinfect medical materials by heating them with radio-frequency waves. A further object or aspect of the invention is to dispose of sterilized medical and veterinary waste in an environmentally safe manner. Additional objects, advantages, and novel features of the invention will be set forth in part in the description which follows, and in part will become apparent to those skilled in the art upon examination of the following, or may be learned by practice of the invention.

BRIEF DESCRIPTION OF THE DRAWINGS

FIGS. 12A, 12B and 12C are plan and front side elevational views of a different type of radio-frequency treatment unit which can be used without the exciter plate, the top and bottom of the shielded cavity serving as termination points for the electric fields, thereby simplifying the cavity design and permitting operation at higher frequencies.

FIG. 14 is a schematic view of a semicontinuous waste disinfection system employing the radio-frequency treatment unit illustrated in FIGS. 6A, 6B and 6C;

DETAILED DESCRIPTION OF THE PREFERRED EMBODIMENTS

Figure 1:
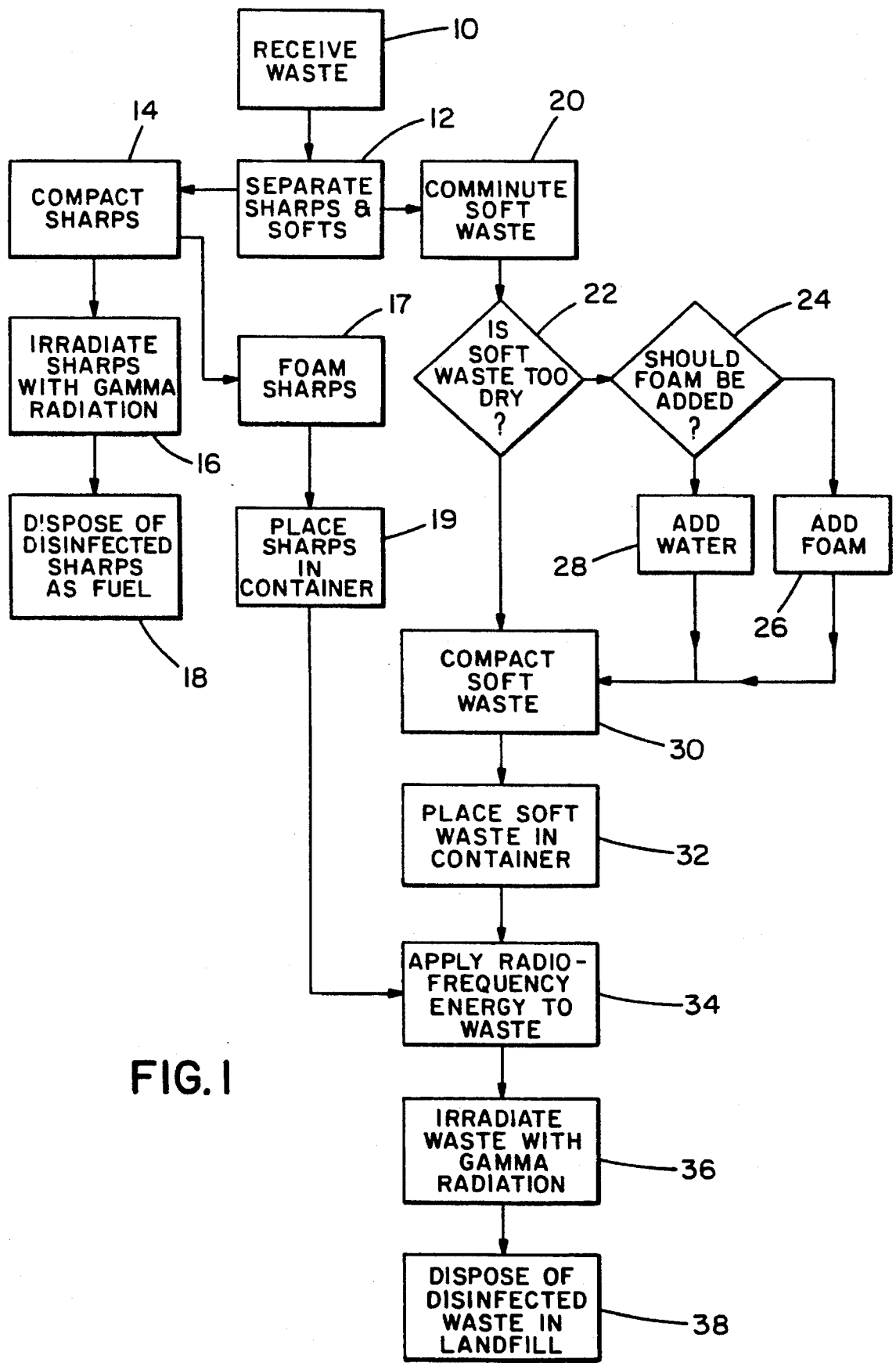
FIG. 1 is a flow diagram of the steps involved in rendering medical waste harmless by heat treatment with radio-frequency electromagnetic fields and irradiation by gamma radiation.
Figure 2:
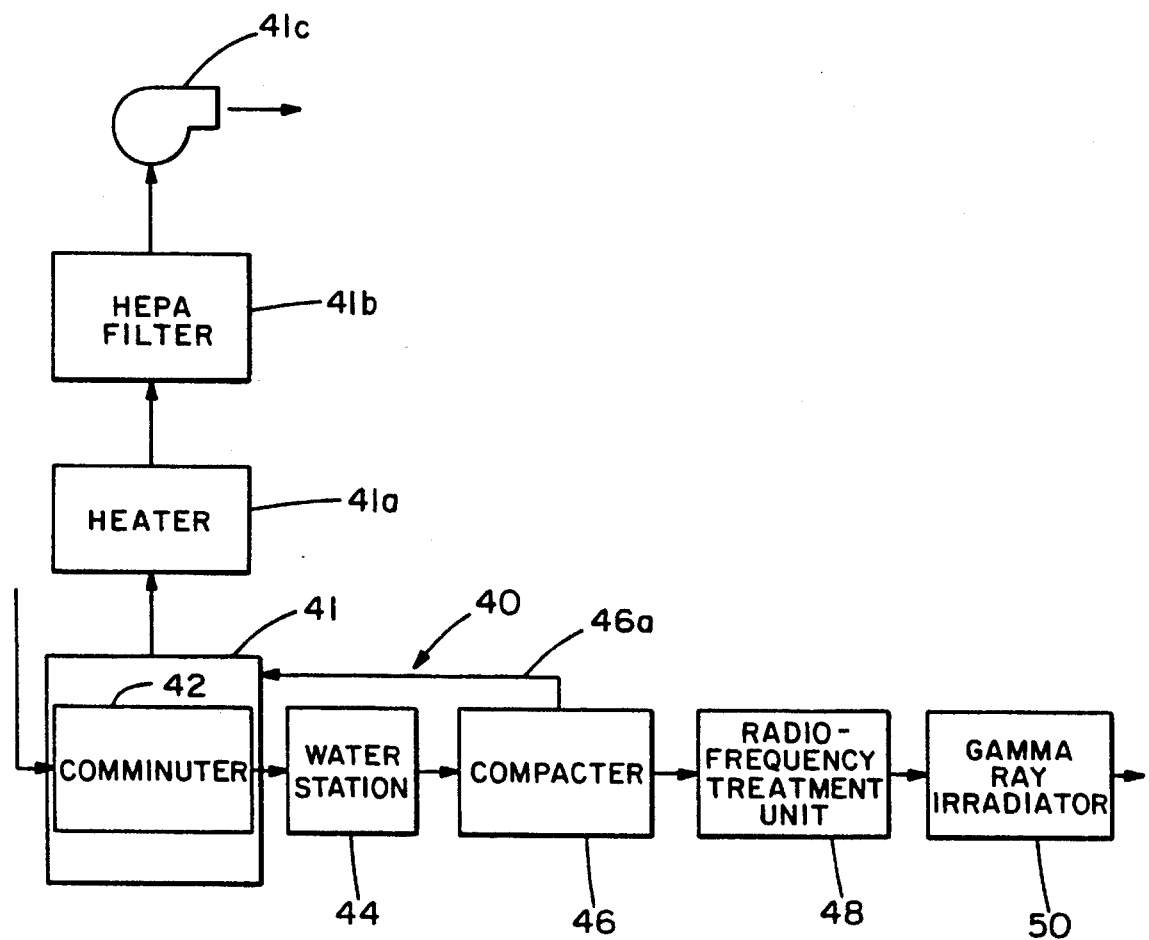
FIG. 2 is a block diagram of an apparatus for disinfecting medical waste by applying radio-frequency energy and gamma radiation.

Referring now to the drawings and especially to FIG. 1, a method of practicing the present invention is shown therein and includes a step 10 of receiving from a hospital or the like medical waste having microorganisms thereon.

In a step 12, the medical waste is examined to determine the sharps content of the medical waste. If the sharps content is relatively high, some or all of the sharps waste may be separated from the soft waste. This is done to control the sharps content of the compacted waste in step 30. Our tests have shown that a soft waste containing up to thirty per cent sharps waste by weight can be heated in step 34 without significant arcing problems.

If sharps waste is separated in step 12, they can be processed in either of two alternative methods. The sharps are comminuted and/or compacted in step 15. Foam or other low-dielectric moisture-containing material is added to the sharps waste in step 17, and are placed in a fire-resistant and vapor-containing container in step 19. The containers are then subjected to radio-frequency in step 34, to gamma radiation in step 36, and are disposed in step 38. As an alternative, sharps waste separated in step 12 may be comminuted and/or compacted in step 14 from about 5 to 10 pounds per cubic foot to up to 28 pounds per cubic foot. The sharp medical waste is then irradiated with a 1.5 megarads dose of gamma radiation to disinfect it and in a step 18, may then be disposed of as fuel or in a landfill.

The soft medical waste is comminuted in a step 20 which results in an increase in the homogeneity of the soft medical waste. A determination is made in a step 22 as to whether the comminuted soft medical waste is too dry. If it is, an additional determination is made in a step 24 as to whether a foam comprised of water and a surfactant, such as detergent, should be added to the comminuted soft medical waste. If the decision is yes, foam is added in a step 26, if the decision is no, water is added in a step 28 in the form of a water spray. The comminuted soft medical waste, with the proper amount of water, is then compacted in a step 30 and placed in an epoxy-fiberglass fire-resistant container in a step 32. The epoxy-fiberglass container containing the compacted soft medical waste has radio-frequency energy applied to it in a step 34 to heat the waste to a temperature of at least 60° C to inactivate viruses therein. The soft waste has its wet portions heated thereby evolving water vapor. The water vapor condenses on the dry portions heating them by the heat of vaporization and from the energy absorbed from the radio-frequency electric field. The heating inactivates viruses thereon. Following such heating, in a step 36, the soft medical waste is exposed to a dose of 0.5 megarads of gamma radiation whereby the bacteria and spores on the soft medical waste are inactivated. The disinfected soft medical waste is then disposed of in a landfill in a step 38.

In order to perform the aforementioned process steps, an apparatus 40 embodying the present invention includes a negative pressure clean room 41 connected to a 70° C. heater 41b for disinfecting air from the clean room 41. A high efficiency particulate air (HEPA) filter 41c is connected to the heater 41b. A blower 41c is connected to the HEPA filter 41b to receive air therefrom and expel it to the environment. A shredder 42 is positioned within the clean room 41 and receives medical waste so that when a quantity of soft medical waste is placed within the shredder 42, it is comminuted or shredded into soft medical waste particles having an average particle size of 1 to 2 inches in linear dimension. In the preferred embodiment a model Dual 1000E from Shredding Systems, Inc. of Wilsonville, Ore. is used. As stated above, the soft medical waste particles are then fed to a water station 44 which may simply comprise a open conveyor or inspection area at which water may be sprayed on the waste particles. The water station 44 may additionally have foaming equipment of a type which is commercially available from Goodway Industries for applying aqueous foam comprising water and detergent to the comminuted soft medical waste to increase its ability to absorb radio-frequency energy and convert the radio-frequency energy into heat. A compactor 46, connected by a negative pressure coupling to the clean room 41, may optionally be used to increase the density of the comminuted soft medical waste from a mean density of five to ten pounds per cubic foot to up to twenty eight pounds per cubic foot. It may be appreciated that the compactor 46 receives not only the soft medical waste which has been previously comminuted but also the sharp medical waste for compaction. Only the soft medical waste, which has been comminuted, wetted and compacted is received by a radio-frequency treatment apparatus 48 to be heated thereby. After the soft medical waste has been heated in the radio-frequency treatment apparatus 48 to a temperature of at least 60° C., at which temperature most of the viruses thereon are inactivated, the soft medical waste is placed in a cobalt 60 gamma ray irradiator 50 of the type which may be purchased from Systems Innovators. The previously heated soft medical waste receives a gamma radiation dose of 0.5 megarads from a cobalt 60 source within the gamma ray irradiator 50. The 0.5 megarads dose of gamma radiation, which is sufficient to inactivate the bacteria and bacterial spores on the soft medical waste following heating to 60° C. in the radio-frequency treatment unit 48.

Figure 9:
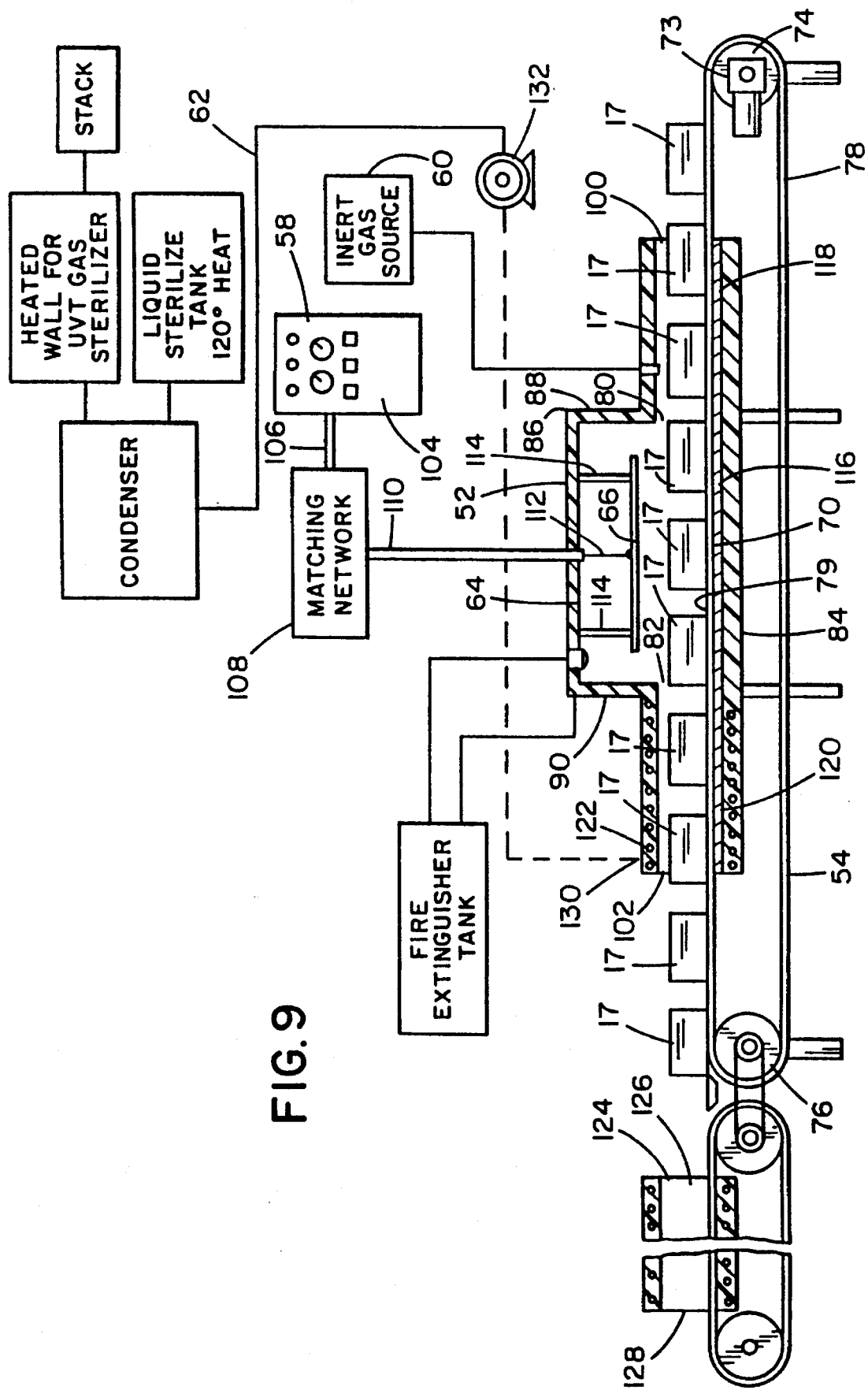
FIG. 9 is a schematic view of a system for continuously disinfecting bagged and boxed medical waste by using radio-frequency energy.

Referring now to the drawings and especially to FIG. 9, the radio-frequency treatment apparatus 48 is generally shown in FIG. 9 and includes a radio-frequency treatment unit 52 and a waste transport system or conveyor 54 for feeding soft medical waste 16 in epoxy-fiberglass container 17 to the radio-frequency treatment unit 52. A source of radio-frequency energy 58 is connected to the radio-frequency treatment unit 52 to energize it and an effluent handling system 62 is connected to the radio-frequency treatment unit 52 to treat gases and vapors evolved during the heating of the soft medical waste 16. Also a source 60 of inert sweep gas, such as nitrogen, is connected to the radio-frequency treatment unit 52 for driving oxygen therefrom to avoid combustion of the medical waste being heated.

The radio-frequency treatment unit 52 includes an applicator or reactor 64 providing a reaction chamber to which radio-frequency energy is applied. The design of the applicator 64 to produce the required electric field and exposure time is of interest. Such applicators may be divided into three basic groups: (1) TEM parallel plate applicators where the wavelength of the excitation frequency is large or comparable to the dimensions of the reactor 64; (2) TE or TM controlled mode applicators where the dimensions of the reactor 64 are comparable to or several times the wavelength of the excitation frequency; and multi-mode TE and TM applicators where the maximum dimension of the reactor 64 is typically four or more times the wavelength of electromagnetic energy having the excitation frequency. Typically with the multi-mode TE or TM applicators, the modes are not controlled such that a number of peaks and nulls of the electric field exist within the heating unit, such as exists typically in a microwave oven.

Figure 8A:
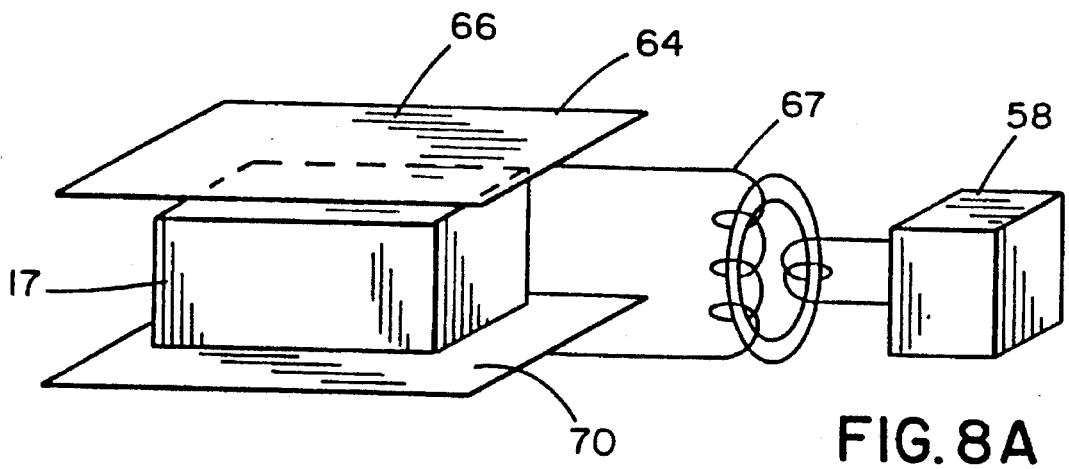
FIGS. 8A, 8B, 8C and 8D are schematic representations of radio-frequency treatment units and radio-frequency energy sources which may be used in the radio-frequency disinfection of infectious medical waste.

FIGS. 8A, 8B, 8C and 8D illustrate the transition from a parallel plate TEM applicator 64 to a controlled limited mode TE or TM applicator. FIG. 8A shows a reactor 64 formed of two parallel plates 66 and 70 with the medical material 16 in the containers 17 placed between the upper and lower plates 66 and 70, respectively. Voltage is applied between the upper and lower plate by means of a tuning coil which is driven from the RF source 58. As long as the wavelength of the applied voltage is large compared to the dimensions of the applicator 64, and the container 17 is well within the extended portions of the metal plates 66, 70, a uniform field can be applied.

Figure 8B:
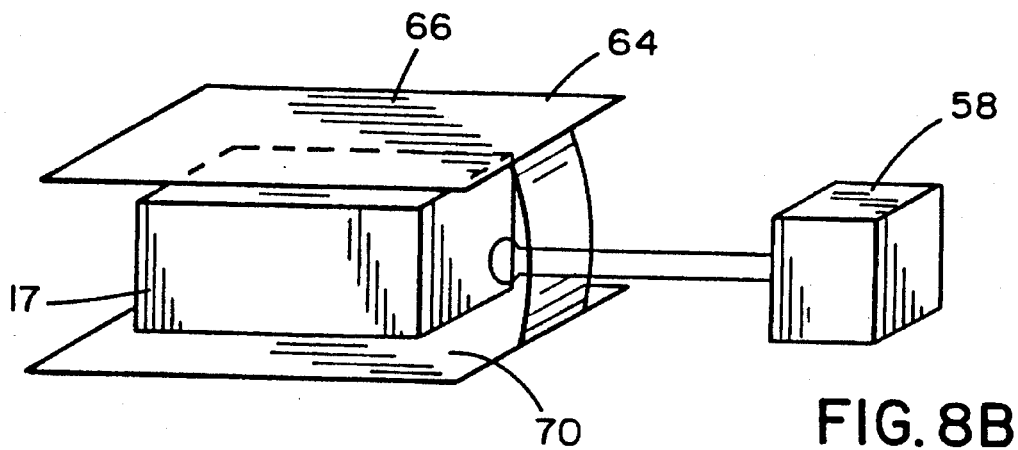
Figure 8C:
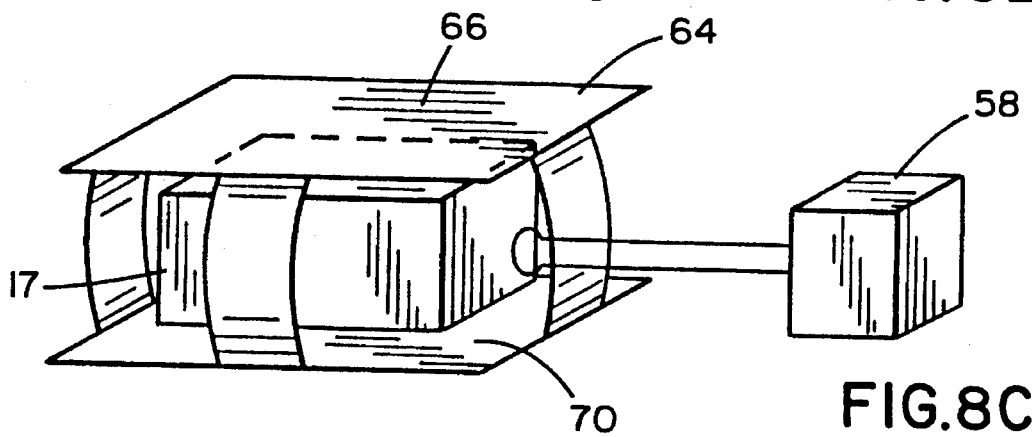
Figure 8D:
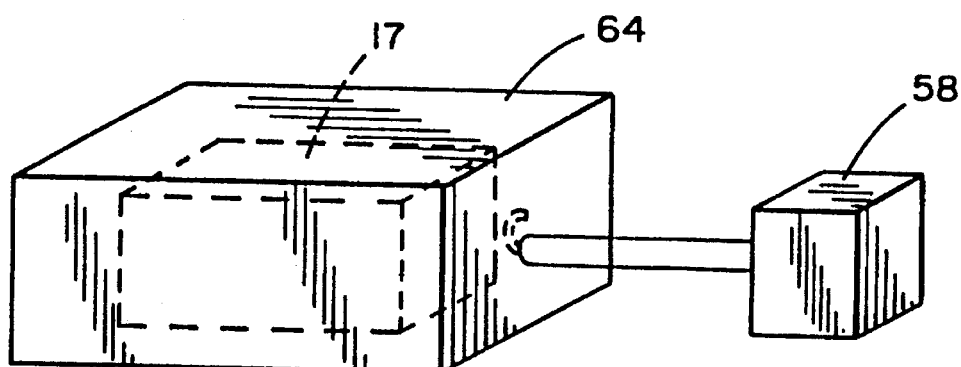

The applicator shown in FIG. 8A is an example of the TEM applicator and is limited to the lower frequencies, and because the dielectric absorption is roughly proportional to the "nth" power of the frequency (wherein ranges from 0.3 to 1.0 for frequencies below about 300 MHz) and the square of the electric field strength, substantially higher electric field strengths for lower frequencies are required to cause the same heating effect as might be expected for higher frequency operation. Higher frequency operation is possible in a controlled mode heating cavity 64 such as shown in FIG. 8D, which is an example of the controlled mode TE or TM applicator. The transition of the reactor 64 from the embodiment of FIG. 8A to that shown in FIG. 8D is illustrated in FIGS. 8B and 8C. The parallel plates 66, 70 shown in FIG. 8A are resonated with the thin wire series inductance 67. However, by reducing the value of this inductance, higher frequency resonances are possible. Nevertheless, there is an upper limit to the frequency at which this resonance can be made to occur if just a single thin wire solenoidal inductor is employed. To increase the resonant frequency, straps 69 on the sides of the two parallel plates 66, 70 can be employed as shown in FIGS. 8B and 8C, with power applied by way of a launching coil or turn 67. Eventually this arrangement is transformed into the controlled mode TE or TM applicator as shown in FIG. 8D. The controlled mode TE or TM applicator 64 is defined where ½ wavelength is comparable to one of the larger dimensions of the box. This limits the number of permissible modes and allows controlled and uniform heating. In the case of a microwave oven, the dimensions are in the order of 6 to 8 half wavelengths. This results in uncontrolled modes and non-uniform heating.

Figure 3:
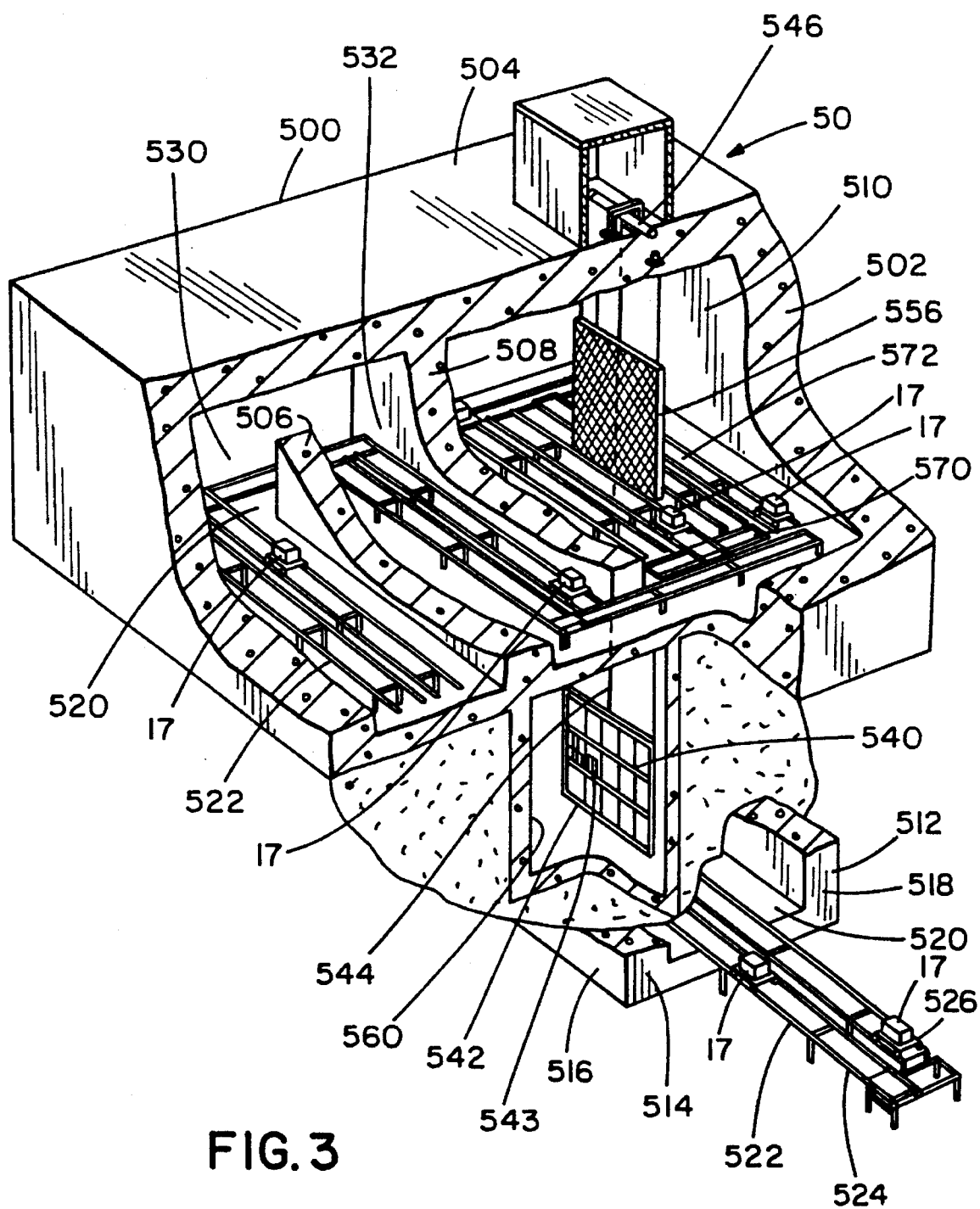
FIG. 3 is an isometric view of a gamma ray irradiation unit having portions broken away to show the details thereof.
Figure 4:
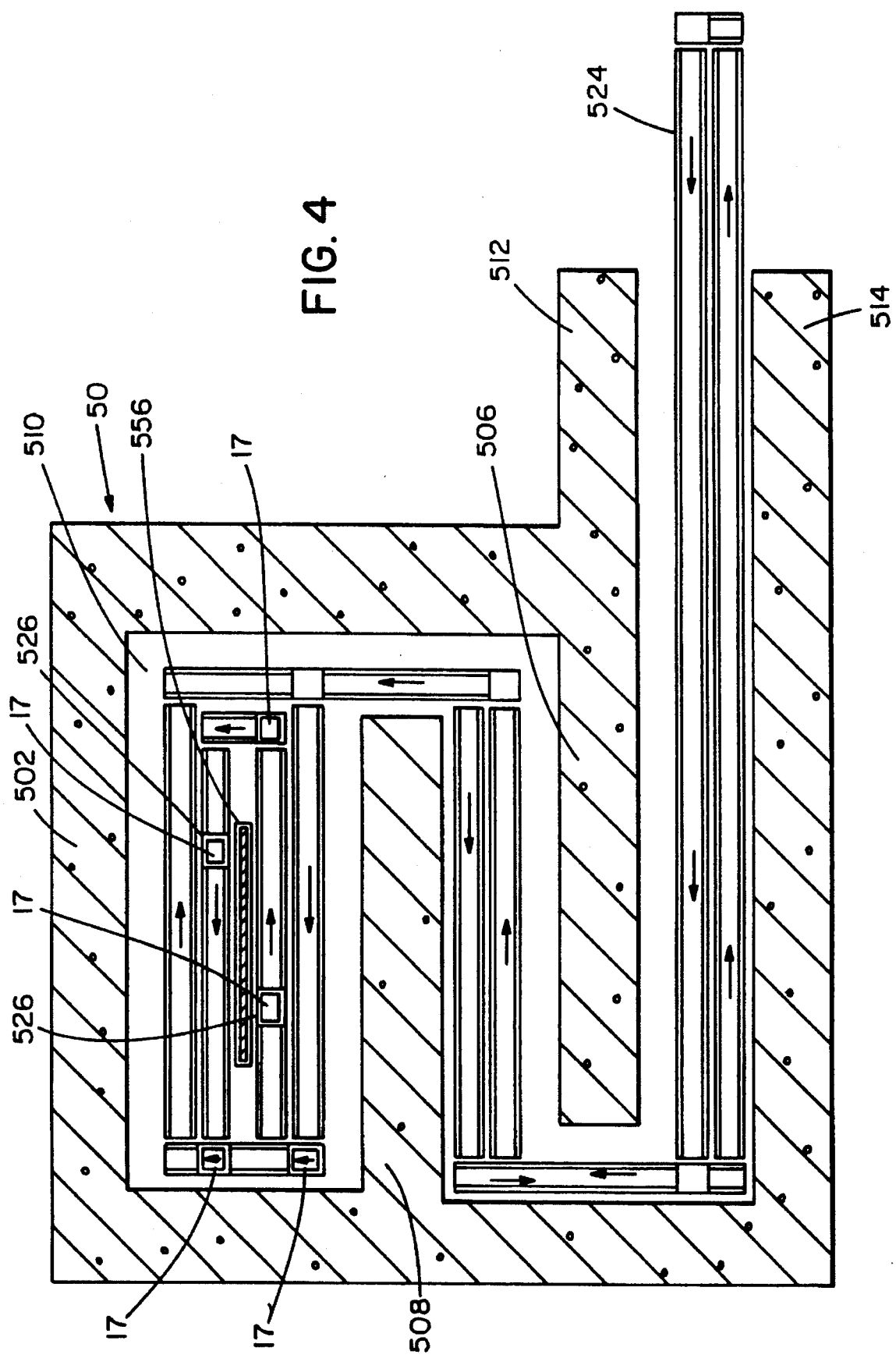
FIG. 4 is a sectional view of the gamma ray irradiation unit of FIG. 3.
Figure 5:
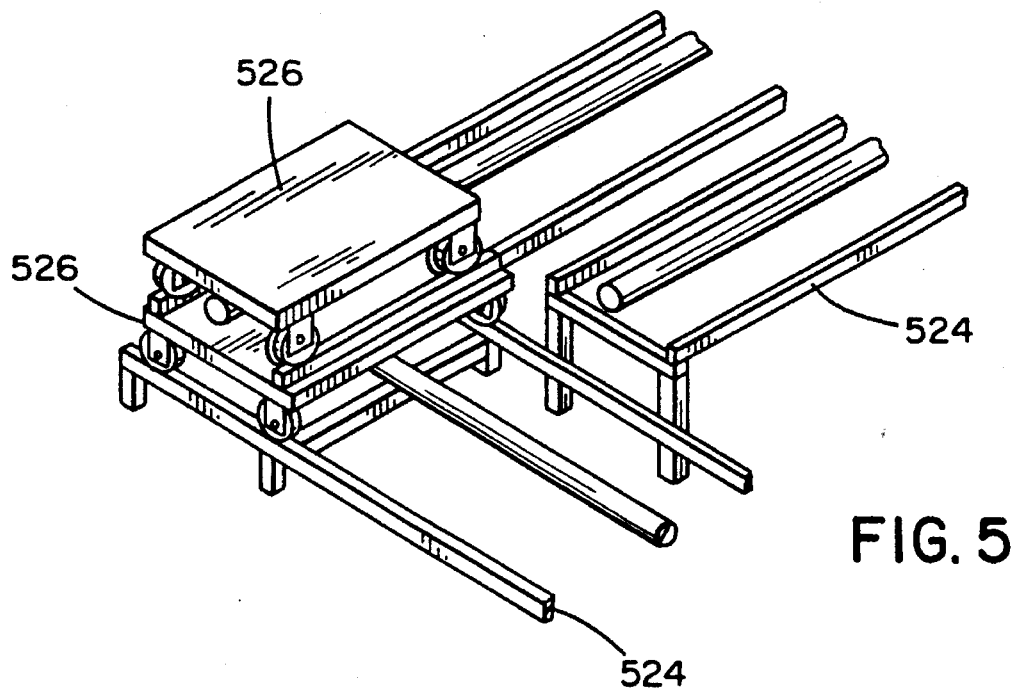
FIG. 5 is an isometric view of a portion of a material handling system of the gamma ray irradiation unit of FIG. 3.
Figure 6:
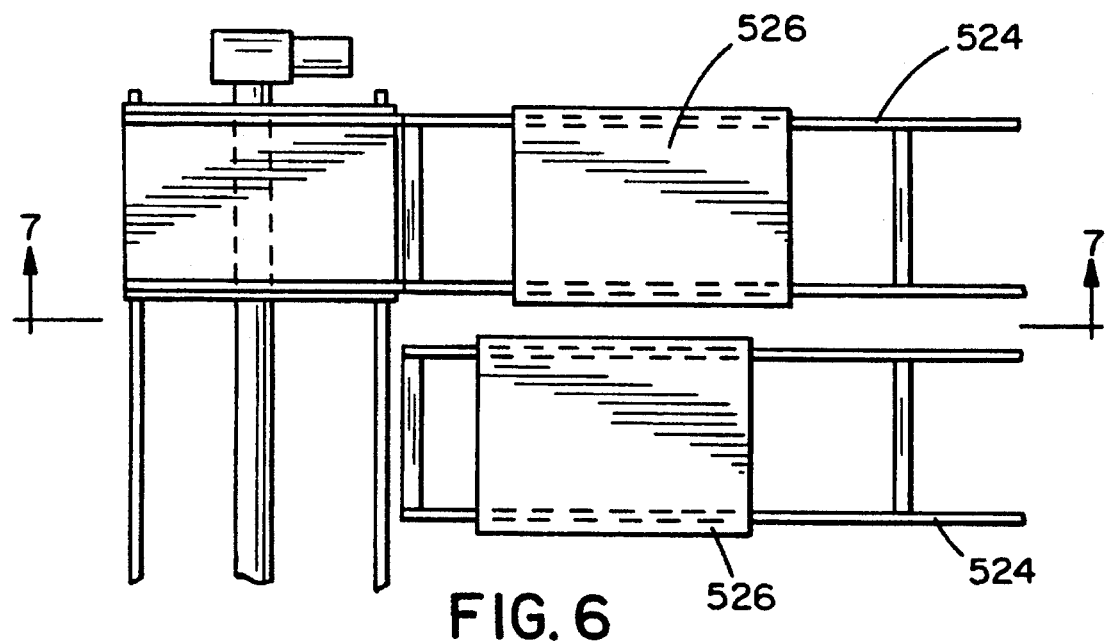
FIG. 6 is a top elevational view of a portion of the material handling system of FIG. 5.
Figure 7:
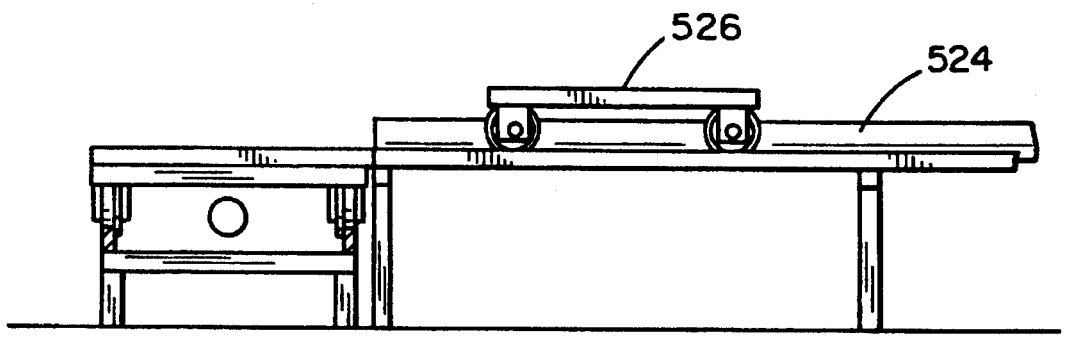
FIG. 7 is a sectional view taken along line 7—7 of FIG. 6 showing further details of the material handling system.

In another embodiment, as may best be seen in FIG. 3, the waste transport system 54 also includes a conveyor motor 72 which drives an input conveyor drum 74.

An output idler conveyor drum 76 also comprises a portion of the conveyor 72 and a conveyor belt 78 engages both the input driven drum 74 and the output idler drum 76. A portion 79 of the conveyor belt 78 extends through the radio-frequency treatment unit 52 for carrying the container 17 of medical waste 16 therethrough for treatment.

The radio-frequency treatment unit 52 comprises the radio-frequency chamber 64 having a radio-frequency chamber inlet opening 80 and a radio-frequency chamber outlet opening 82. The radio-frequency treatment unit 52 has a length of 18 meters, a width of 4.5 meters and a height of 3 meters. The radio-frequency chamber 64 comprises a bottom wall 84, a top wall 86, an inlet wall 88, an outlet wall 90, a first side wall 92, and a second side wall 94. Each of the chamber walls is constructed of highly conducting material such as copper or aluminum. Typically 6 millimeter thick aluminum can be used, which allows the chamber walls to be self-supporting. Also 3 millimeter thick copper could be used in conjunction with additional physical support. The radio-frequency treatment unit 52 also includes an inlet tunnel 100 connected to the inlet wall 88 at the inlet opening 80. The inlet tunnel 100 has a rectangular cross section and is dimensioned to act as a wave guide below cutoff to prevent the radiation of electromagnetic fields from the interior of the radio-frequency chamber 64 to the environment while allowing the medical waste 16 to be carried freely into the radio-frequency chamber 64 by the conveyor belt 54. Likewise, a wave guide below cutoff forms an output tunnel 102 from the outlet 82 at the outlet wall 90 to carry medical waste 16 out of the vicinity of the radio-frequency treating chamber 64 without allowing radio-frequency energy from the radio-frequency treating chamber 64 to leak into the surroundings.

In order to energize a radio-frequency electromagnetic field and, in particular, the time-varying electric field component thereof, within the radio-frequency treating chamber 64, the radio-frequency energy generator 58 is provided and includes a radio-frequency current generator 104 connected to a coaxial cable 106 for feeding power therethrough. A matching network 108 receives the radio-frequency energy from the coaxial cable 106 to which it is connected. A second coaxial cable 110 is also connected to the matching network 108 to carry the radio-frequency power therefrom. That coaxial cable 110 has a center lead 112 which penetrates the top wall 86 of the radio-frequency chamber 52 and is connected to the vertically movable substantially rectangular conductive exciter plate 66. The outer conductor is connected to the top wall 86 and grounded. The exciter plate 66 is suspended by a plurality of nonconductive ropes 114, preferably nylon or orlon, from the top wall 86 of the radio-frequency chamber 52. This allows the exciter electrode 66 to be moved with respect to the container 17 of medical waste 16 to provide a spatially uniform, time-varying electric field to heat the medical waste 16 relatively uniformly. A three millimeter thick copper bottom plate 116, which is substantially flush with a pair of bottom plates 118 and 120 of the inlet and outlet wave guide below cutoff tunnels 100 and 102, respectively, comprises the bottom plate of what is in essence a biplate configuration reactor. Typically, the bottom plate 116, as well as the walls 84, 86, 88, 90, 92, and 94 of the radio-frequency chamber 52, are maintained at ground potential while the exciter plate 66 is excited by the radio-frequency energy fed through the coaxial cable 62.

It is particularly important in the practice of the present invention that the exciter plate 66 be movable, as this allows adjustment of the relatively uniform portion of the electric field within the radio-frequency chamber 52. This is important because the size of the containers 17 containing the medical waste 16 may vary from time to time. It is important that when the containers 17 are traveling through the center portion of the radio-frequency heating chamber 64, they be subjected to a substantially spatially uniform time-varying electric field so that the contents thereof are uniformly heated.

Figure 10:
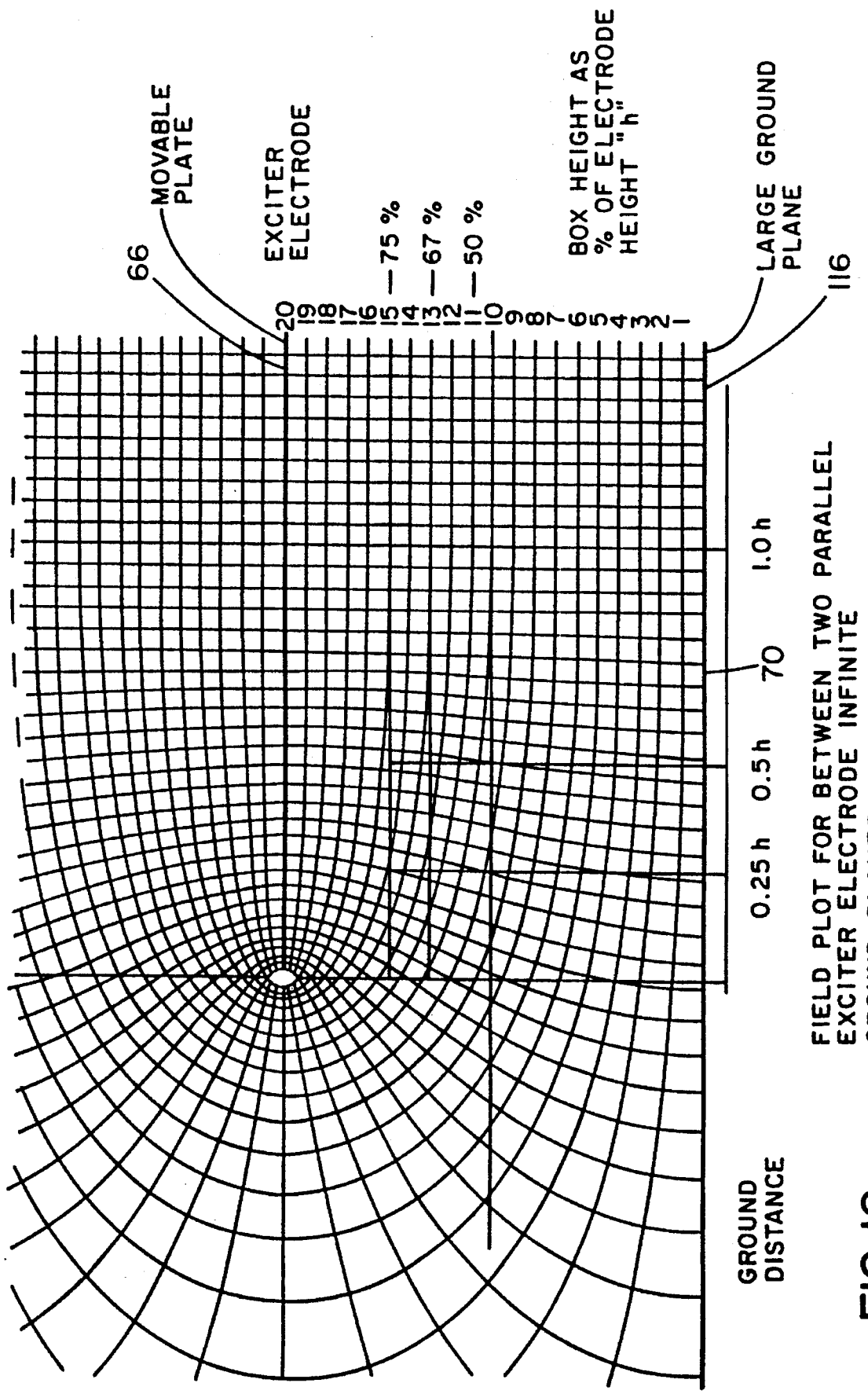
FIG. 10 is a section of a radio-frequency reactor of FIG. 3, showing the electric field vector lines and equipotential lines generated within the radio-frequency treatment unit.
Figure 11:
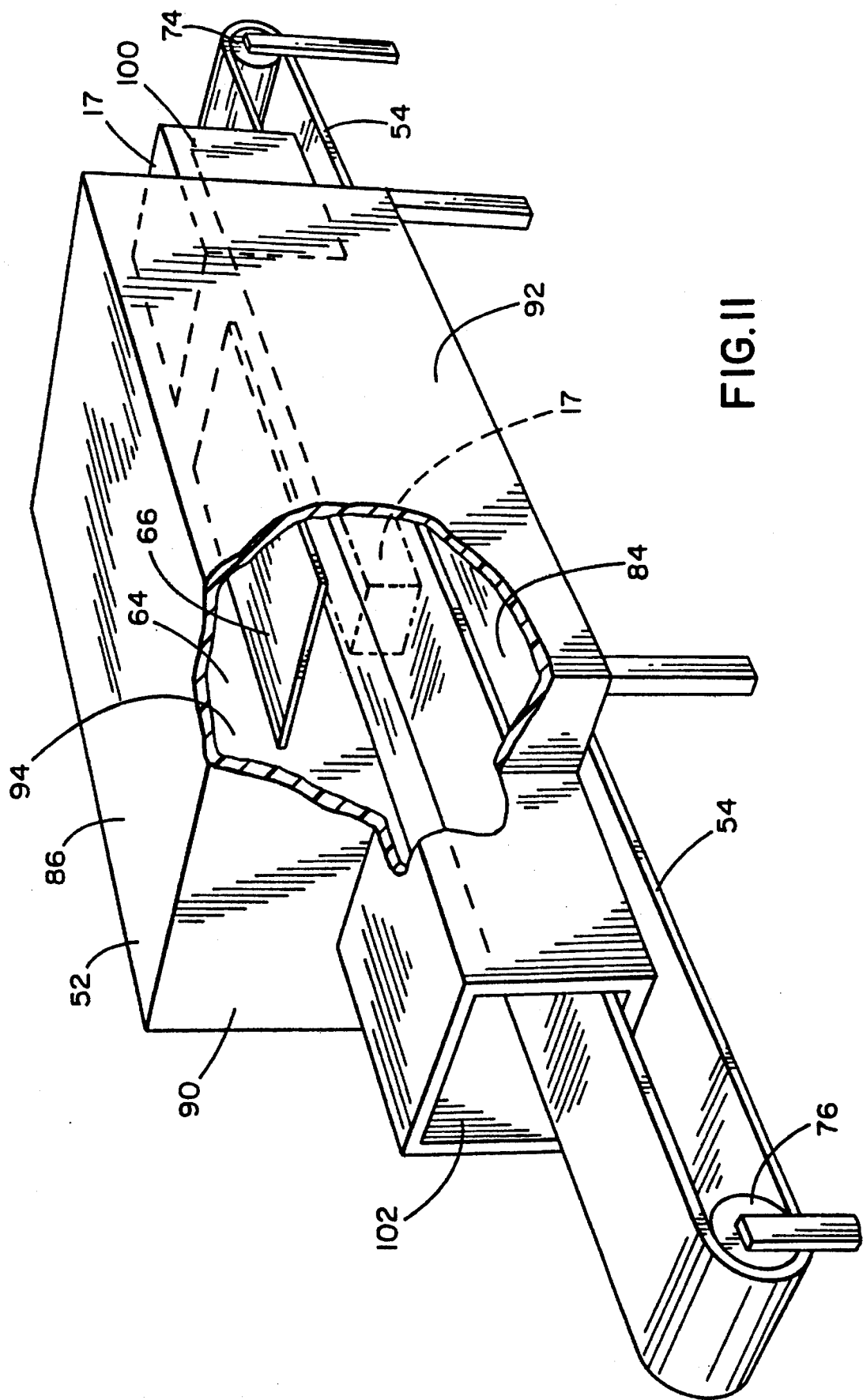
FIG. 11 is an isometric view of the radio-frequency treatment unit of FIG. 3 and a conveyor associated therewith showing details of the orientation of the conveyor with respect to an exciter plate within the reactor and the radio-frequency treatment unit.

In the case of the parallel plate exciter, the dimensions of the box 17 compared with the dimensions of the electrode 66 are important in order to assure reasonably uniform electric field and resultant heating effects. To determine the relationship between the box dimensions and the size of the electrode exciter, the data in FIG. 10 were developed. This shows equi-potential lines (horizontal) coupled with the displacement current lines (near-vertical) for a limited extent exciter electrode 66 centrally located in a large conducting box. The relative electric field at any location can be developed by determining the dimensions of a square at any location and a similar square in the uniform region (far right) and dividing the maximum dimensions of this uniform field square by a similar dimension of the square at the desired location.

It can be seen therefore, if the guard distance, that is the distance from the edge of the box to the downward projection of the edge of the electrode, is equal to the height of the electrode, that very little field distortion occurs and that the electric field in the region to the right of this point is reasonably uniform. Further studies show that if the edge of the box is moved farther to the left, field distortion occurs such that the electric field is significantly less near the ground plane and therefore the material of the box would experience a significantly lower heating rate. Guard distances which are equal to about one-fourth or less than the height of the exciter electrode are relatively unsatisfactory.

On the other hand, it is seen that as the height of the box is increased, the field distortion near the edge of the electrode is such as to contribute excess field intensities, particularly where the height of the box is 75% of that of the exciter electrode and the guard distance is equal to one-quarter of the electrode height. Data taken from this plot are summarized in Table 1. It may be seen that guard distances as little as one-fourth the height of the electrode are acceptable but, on the other hand, the maximum height of the box probably should preferably be no more than 67% of the height of the exciter electrode. The reason for this is that as the box enters from the left going into the right, it encounters increasingly high levels of electric field near the edge of the electrode. As a consequence, excess field intensity can occur there which can lead to potential gradients and arcing phenomena. To ensure against such effects as well as over or under heating, the normalized heating rate during entry wear the top edge of the box should not vary more than 1.5 to 1.0 for the parallel plate type of heater shown in FIG. 3. Where the bulk of the water is not evaporated but rather repositioned, heating ratios of 2.0 to 1.0 can be tolerated. Where the bulk of the water is evaporated and heating is contained beyond the vaporization point, the heating rate variation should be less than 1.5 to 1.0.

TABLE 1

HEATING POTENTIAL ($E^2$) NORMALIZED TO THE HEATING POTENTIAL IN THE UNIFORM FIELD REGION AS A FUNCTION OF THE BOX HEIGHT RELATIVE TO THE HEIGHT OF THE ELECTRODE AND FOR RELATIVE GUARD LENGTHS.

| Dimensions Relative to Electrode Height, h | | Normalized Heating Potential, ($E^2$) | |
|---|---|---|---|
| Box Height | Guard Length | Top of Box | Bottom of Box | Top of Box During Entry |
| 0.5 | 0.5 | 0.92 | 0.96 | 1.0 |
| 0.5 | 0.25 | 0.92 | 0.88 | 1.0 |
| 0.67 | 0.5 | 1.25 | 0.96 | 1.21 |
| 0.67 | 0.25 | 1.10 | 0.88 | 1.21 |
| 0.75 | 0.5 | 1.44 | 0.96 | 1.8 |
| 0.75 | 0.25 | 1.2 | 0.88 | 1.8 |

In the present embodiment, in particular for the type of reactor shown in FIG. 9, a 12 megahertz radio-frequency current generates a 12 megahertz radio-frequency electric field within the radio-frequency chamber 64 to heat the medical waste 16 within the hospital waste containers 17. It may be appreciated that the hospital or medical waste 16 may comprise a wide variety of waste having many different dielectric constants. For instance, the sharps will include metals in which collected displacement currents will be induced by the time-varying electric field. Very moist materials will also be included, as well as quite dry materials such as gloves and the like. In particular, the moist materials couple well with the radio-frequency field due to the fact that the dipole moments of the water molecules cause the water molecules to have a torque exerted thereon by the electric field when it is unaligned with the dipole moments. This causes the molecules to be moved, in particular rotated by the field. The water molecules then transfer disordered kinetic energy to the materials upon which they are in contact, causing them to be heated.

When the medical waste 16 is first placed in the radio-frequency chamber 64, the wet portions of the medical waste 16 are rapidly heated by the radio-frequency energy, causing water vapor to be evolved therefrom. The water vapor is dispersed by convection and diffusion throughout the bags of hospital waste and condenses on the dry waste therein, due to the fact that the dry waste has been relatively unheated until it comes in contact with water. The condensation of the water vapor on the cooler material transfers heat thereto by giving up heat of vaporization. More importantly, however, the condensed vapor wets the formerly dry material whereby the water is volumetrically heated by the time-varying electric field, thereby generating thermal energy in the previously dry waste and causing the waste within the container to be substantially uniformly volumetrically heated. Since the frequency of the time-varying electric field is selected to be 12 megahertz, or, in the alternative 64 megahertz, the electric field penetrates well into typical waste bags, and the entire volume of medical waste within the bags is substantially uniformly heated once the water is dispersed, allowing the waste to be rapidly heated. Once a minimum temperature of about 90° C. is reached, virtually all pathogenic organisms are all destroyed by the heat, and the waste is disinfected.

In one embodiment of the invention, as shown in FIG. 9, the exit tunnel 102 is lined with electric resistance heaters 122, which are means for heat soaking the medical waste, if a further margin of safety is desired. As the containerized medical waste 16 passes through the exit tunnel 102, the electrical resistance heaters 122 transfer sufficient heat energy via radiation to prevent heat loss from the containers 17. This heat is not sufficient to raise the temperature of boxes 17 further, but it is only sufficient to maintain the temperature of the boxes 17 at the exit. As a result, the exit tunnel 102 in combination with a similar tunnel 124 of much longer length will provide a means for heat soaking the medical wastes over the appropriate period of time. This can be done with a relatively low power consumption in order to hold the medical waste at the desired temperature for up to approximately 45 minutes. In addition, such a heating tunnel in combination with the RF source heating method provides a means to heat the medical waste in a controlled manner such that combustion does not occur and the plastic does not melt or partially pyrolyze. It would, of course, be difficult, if not impossible, to use such electric resistance heaters or other infrared radiative heaters solely to heat bulky materials like the hospital waste from ambient temperature due to the fact that infrared heaters provide essentially surface and not volumetric heating. That is, in accordance with the present invention, the waste is first heated volumetrically to the desired temperature and held at that temperature by surface heating. If the surface is maintained at the desired temperature, the interior cannot cool.

Doors may be provided at the distal ends of the inlet wave guide below cutoff 100 and the outlet wave guide below cutoff 102 as well as the heat soak entrance 126 and exit 128 to trap gases generated by the heating within the unit. These gases might, like the contents of the medical waste containers 17, be combustible. As a result, the inert gas system 60 floods the radio-frequency heating chamber 64 as well as the inlet tunnel 100 and the outlet tunnel 102 with nitrogen. The flow is a counter flow in the inlet tunnel 100 keeping oxygen out of the system in order to prevent fires. The nitrogen flush also provides other important features to the invention. Since the injection point for the nitrogen flush is near the inlet tunnel 100, or actually on it, the relatively cool nitrogen enters the radio-frequency treating area at approximately the same temperature as the medical waste 16. Nitrogen is carried in the same direction as the medical waste 16 and is heated thereby by conduction, radiation and convection from the heated medical waste 16. As a result, an effective temperature ramp is provided from the inlet portion of the radio-frequency heating chamber 64 to the outlet portion by the flowing of the gas in combination with the gradual heating. Due to the fact that the gas flows in the direction in which the temperature is increasing, refluxing of any vapors released from the medical waste 16 is prevented to the cooler input hospital waste by the directed flow of the nitrogen gas and thus prevents condensation on the cooler exterior of the containers, which could inhibit volumetric heating. The nitrogen gas also operates as a sweep gas and carries effluents out through an effluent exit port 130 which comprises a portion of the inert gas system 60. The effluent exit port 130 is connected to a blower 132 which is connected to the effluent treatment system 62.

Figure 15:
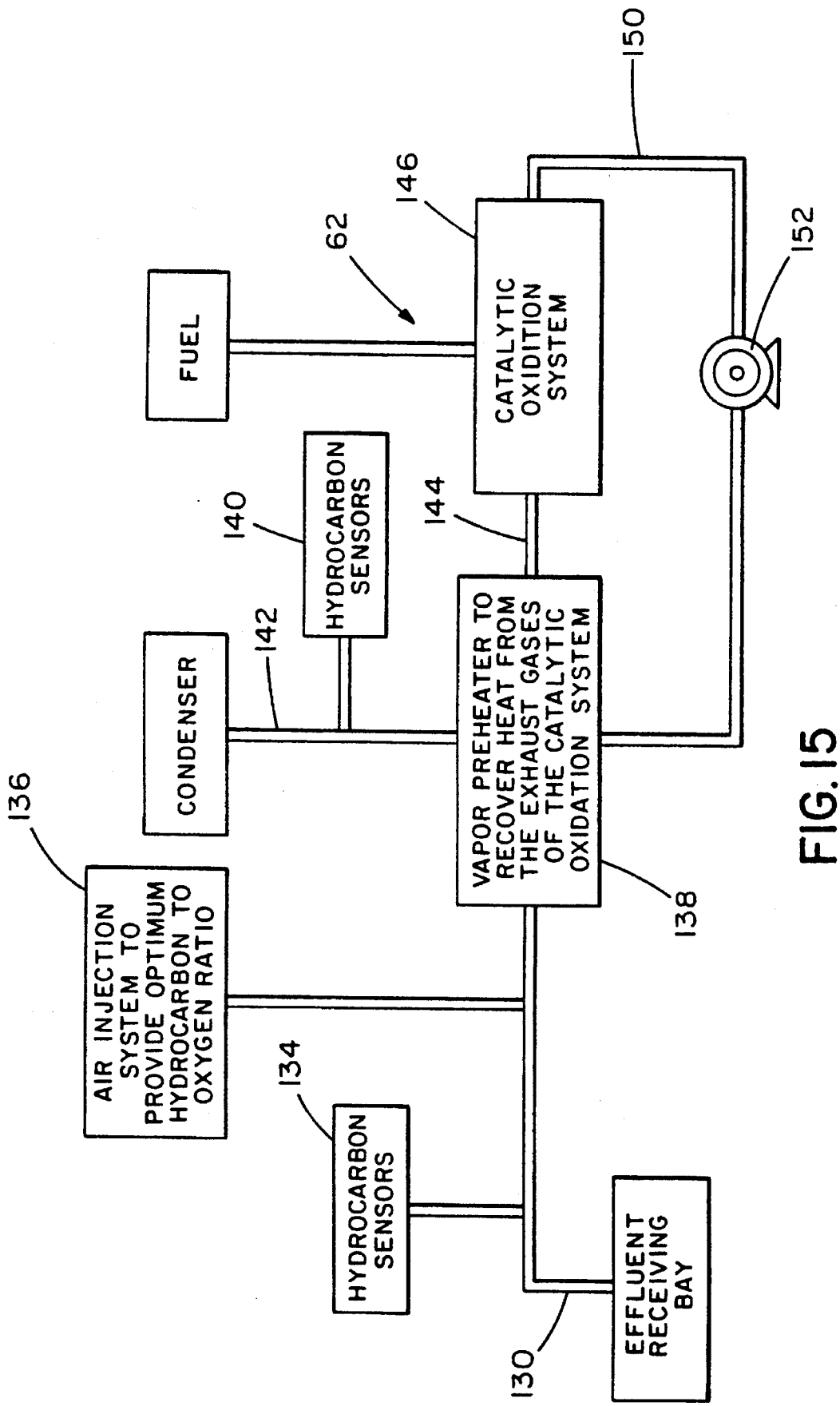
FIG. 15 is a diagrammatic view of the vapor treatment system associated with the apparatus shown in FIGS. 3 and 8.

The effluent treatment system 62, as may best be seen in FIG. 15, processes the effluents evolved in the heating of the infectious medical waste. These effluents essentially consist of steam, air and inert gases, such as the nitrogen sweep gas, as well as some hydrocarbons generated during heating of the waste and possibly pathogens that might have been released during the waste processing. Under normal conditions, though, all of the pathogens would be inactivated or destroyed by the radio-frequency heating. The effluent exits through the duct from the radio-frequency heating chamber 64 and passes a hydrocarbon sensor 134 connected to the duct 130 for determining whether hydrocarbons are present. If hydrocarbons are present in excess of a predetermined value, an air injection system 136 injects air into the effluent gas stream so that a combustible mixture of air and hydrocarbons, as well as inert gases, is fed to a vapor preheater 138. The vapor preheater 138 is a heat exchanger fed with exhaust gases from downstream equipment. A hydrocarbon sensor 140 is connected to a condenser or output duct 142 adapted to receive an inlet from the condenser. The gases are then fed through a duct 144 to a catalytic oxidation system 146 which may be purchased from Allied Signal UOP or other commercial suppliers. The catalytic oxidation system receives fuel such as propane or natural gas, if needed, via a fuel delivery line 148. The catalytic oxidizer 146 also includes a catalyst, such as Torvex catalyst available from Englehart, for the oxidation of hydrocarbons into carbon dioxide and water. The oxidizable components are oxidized by contact with the catalytic oxidizer and resulting hot combustion products are fed through a combustion output line 150 to a blower 152 which directs the hot combustion products through a hot gas output line 154 into the heat exchanger 138 to conserve heat energy by transforming heat from the hot combustion products, before they are vented to the environment, to the effluent gases in the input duct 130. The combustion products are then vented through the output duct 142 to the environment. The hydrocarbon sensor 140 will signal an alarm if unburnt hydrocarbons are passing through the output duct 142, causing a system shutdown to allow correction or alteration of the system parameters to ensure complete combustion of all combustible effluents. The combustion of the combustible effluents also destroys any pathogens which may be trapped therein and which had remained active before combustion.

Figure 16:
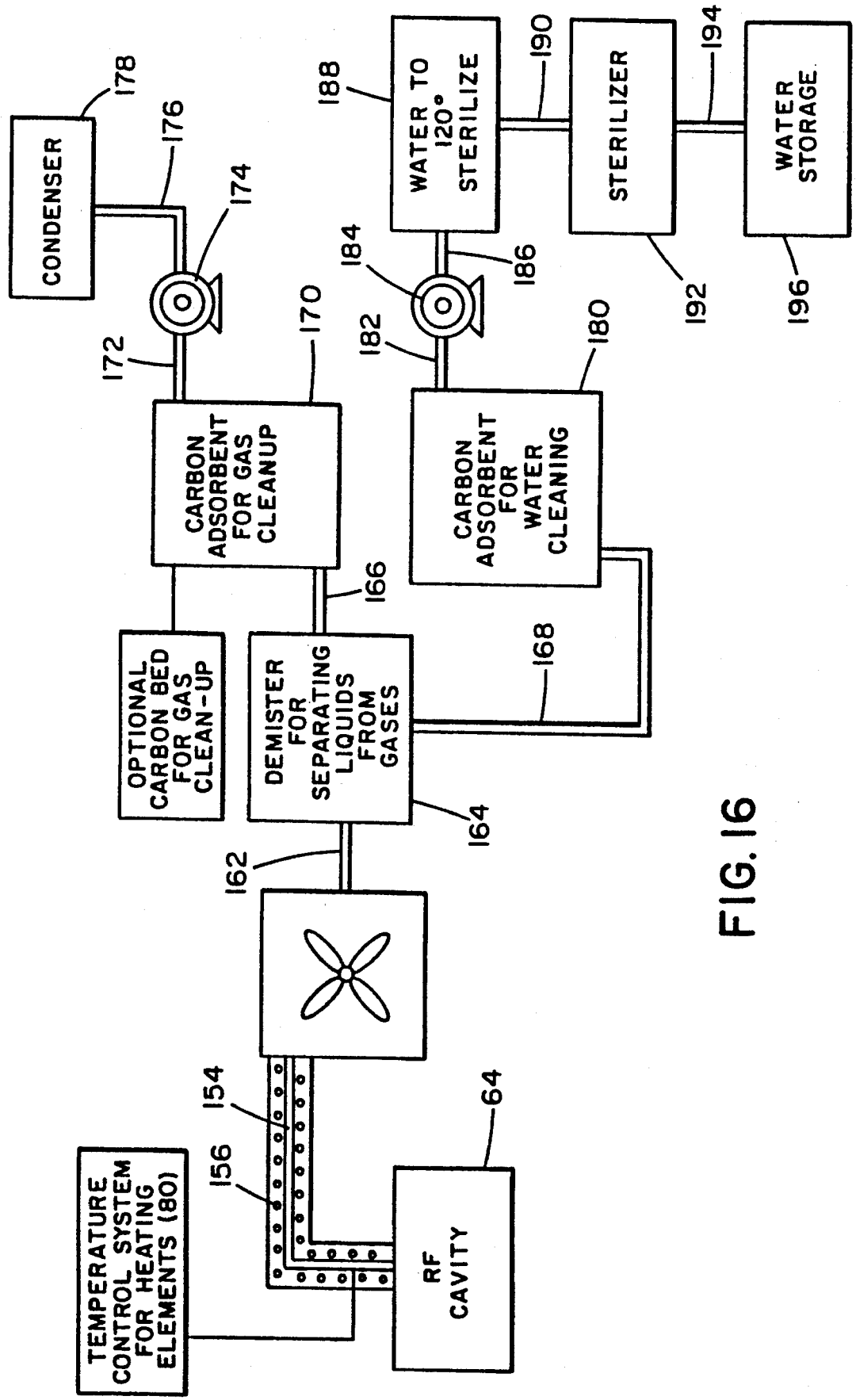
FIG. 16 is a diagrammatic representation of an alternative vapor treatment system employing condensation and waste treatment.
Figure 17:
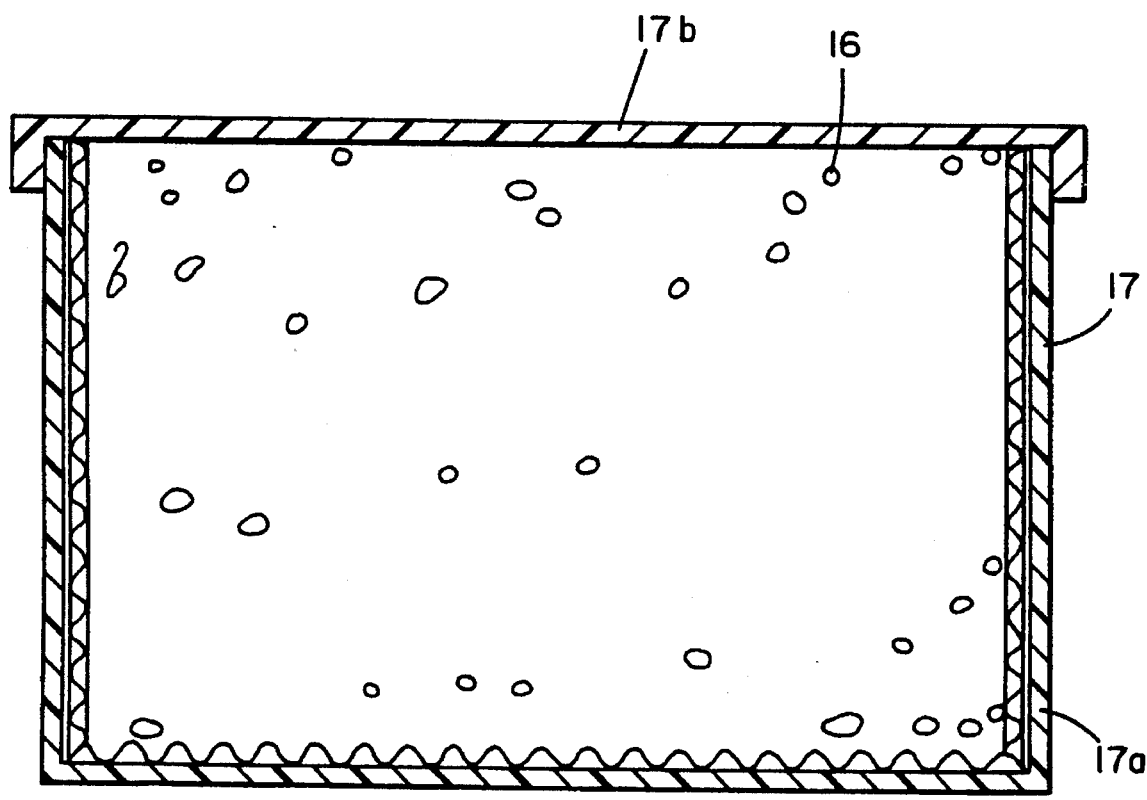
FIG. 17 is a sectional view of an epoxy-fiberglass container holding medical waste.

In an alternative system, the radio-frequency chamber 64, as may best be seen in FIG. 16, is connected to an effluent output line 154 having electrical resistance heating elements 156 wrapped thereabout to maintain a high temperature of the output effluent, thereby preventing any heavy fractions from condensing within the duct 154 and also disinfecting the effluents. Thermal insulation 158 is also wound about the heating elements 156 to prevent excessive heat loss from the electrical heating elements and also to prevent condensation of heavy fractions within the duct 154. An air cooled vapor cooling system 160, which in the alternative may be water cooled, causes condensation of heavy fractions into liquid which may then be passed by a duct 162 to a demister 164. The demister 164 separates any remaining gas flowing through the duct 162 into a gaseous fraction which is fed on a gas line 166, and a liquid fraction fed via a liquid line 168. A carbon adsorbent system 170 receives the gas from the line 166 and vents any inert gases left over through a line 172 which is connected to a venting blower 174. The venting blower 174 feeds the remaining inert cleaned gases through an output duct 176 to the environment or to a condensor 178. Similarly, the liquids are fed via the duct 168 to a liquid adsorbent system 180 which is filled with a commercially available adsorbent material for water cleaning, such as Filtrasorb from Calgon. As an added precaution, clean water is then fed via duct 182 to a pump 184 which passes the clean water through a pipe 186 to a sterilizer 188 which heats the water to 90° C. to 120° C. for sterilization. The sterilized water is fed via a duct 190 to a second sterilizer 192, then through a pipe 194 to a receiving container 196 which receives and stores it. The sterilized water may then be disposed of in an appropriate manner.

As may best be seen in FIG. 14, an alternative semicontinuous waste system 200 is shown therein, utilizing the radio-frequency system. The semicontinuous waste disinfection system 200 includes a radio-frequency waste treater 202 and a waste transport system 204. A radio-frequency energy generator 206 is coupled to the radio-frequency waste treating reactor 34. In operation, the radio-frequency energy generator 206, which includes a control system 208 connected via a cable 210 to a radio-frequency power source 212, generates radio-frequency energy in response to control signals from the control 208 and feeds the radio-frequency energy via a cable 214 to a matching network 216. The matching network 216 has a power delivery cable 218 connected to it which has an inner conductor 220 terminating at a field exciter 222 of a loop type or other suitable type. A dielectric plug 224 terminates an end of an insulating jacket 226 of the coaxial cable 218 and mates with an upper wall 203 of the radio-frequency waste treating reactor 202. The radio-frequency waste treating reactor 202 also includes a bottom wall 232, an inlet wall 234, an outlet wall 236, and a pair side walls, one of which is shown as a first side wall 238. Coupled to the treatment chamber is an inlet wave guide below cutoff tunnel 240 which is substantially rectangular in cross section, connected at an inlet 242 to the reactor 202. The reactor 202 also includes an outlet 244 formed in the wall 236 to which is conducted an outlet tunnel 248 which comprises a radio-frequency wave guide below cutoff. The system may also include an inert gas source as well as an effluent handling system as shown in FIG. 9, although for simplicity such are not shown in FIG. 14.

The conveyor system or waste transport system 204 includes an electric motor 250 controlled by signals carried on a cable 252 from the control 208. The motor 250 drives an input drum 252 of the conveyor system which in turn drive a conveyor belt 254. An output drum 256 also engages the belt 254 in a conventional fashion.

In many cases, especially if pressurization at near atmospheric levels is employed and if heating beyond the vaporization temperature of the dry medical material is required, the total energy or "dose" applied to the medical waste must be controlled. Energy should be sufficient to accomplish the desired final temperature with some additional safety margin. This may result in some of the medical material being overheated beyond the desired final temperature of approximately 60° C. However, too little energy can result in underheating some portions of the medical material and too much energy can result in excessive energy consumption along with partial or complete pyrolysis of the medical waste. Excessive waste also generates noxious gases and thereby burdens the effluent treatment system.

To mitigate these problems, as shown in FIG. 8 sensors 237a and 238b are used to determine the moisture content and/or the presence of sharps. Previously the material may have been weighed and the weight data supplied to the control unit 208 via a cable 239. The control unit 208 then programs the exposure level and controls this via the electric field sensor 234 and the duration of the exposure by sequentially activating the belt 254 via the line 252 and the motor 250. A sensor 237d remotely monitors the temperature of the material in the container 17 by monitoring the infrared or longer wavelength electromagnetic emissions from the material being heated. The sensor 237e monitors the gaseous effluent so as to limit excessive pyrolysis.

Additional wall insulation and/or wall heating may also be employed to suppress heat losses due to convection and diffusion. This is especially desirable if heating above the vaporization temperature is needed. Additional wall and panel insulation 241 along with a wall and a panel heater 343 may be employed. The wall and panel heater 343 is also controlled by the control system 208.

For those cases where heating above the vaporization point of water is employed, it is especially important that the chamber be filled with an inert gas such as nitrogen. The means for the injecting the nitrogen in and keeping the oxygen out are described for the system shown in FIG. 9. For the semicontinuous system shown in FIG. 14, less care is needed in controlling the direction of sweep gases. However, if a continuous version of FIG. 14 is employed, the direction of sweep gases should be from the cooler material to the hotter material as discussed in the embodiment shown in FIG. 9.

The container 17 may then be carried, after treatment by the radio-frequency energy, to the outlet tunnel 248 where electrical resistance heaters 306 provide heat soaking to the container 17, holding it at the desired temperature for a specified period of time in order to provide extra assurance of the destruction of pathogens in the infectious medical waste.

Figure 13A:
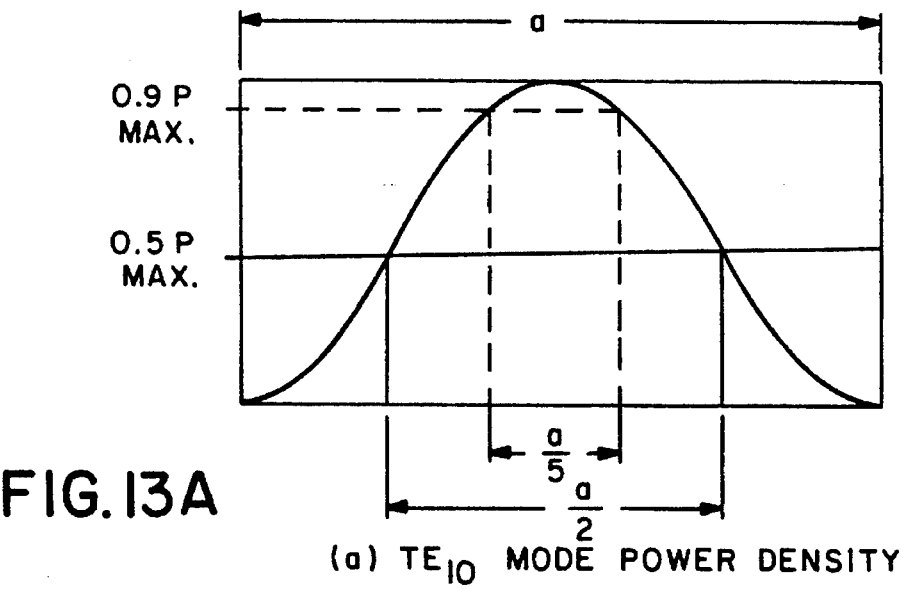
FIGS. 13A, 13B and 13C are graphs of a normalized frequency power density in a single-end driven radio-frequency treatment unit and a radio-frequency treatment unit driven at opposite ends by radio-frequency energy having two different frequencies to provide uniform average power throughout a major portion of the treating chamber of the unit.
Figure 13B:
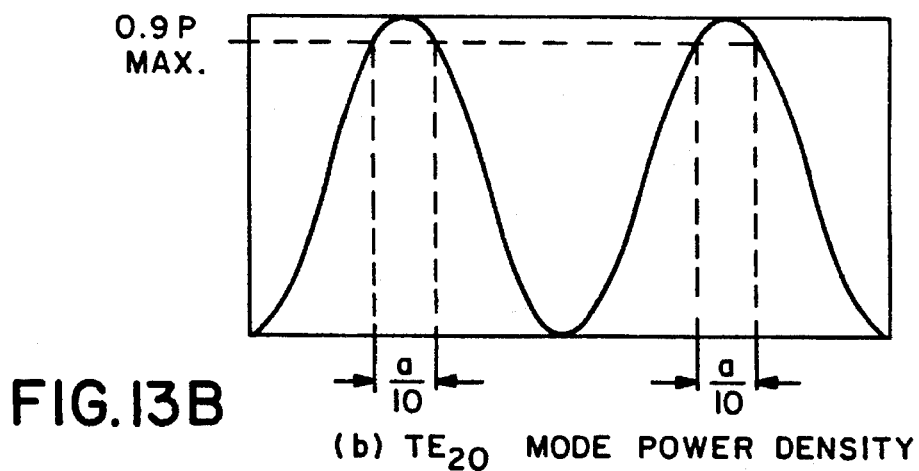
Figure 13C:
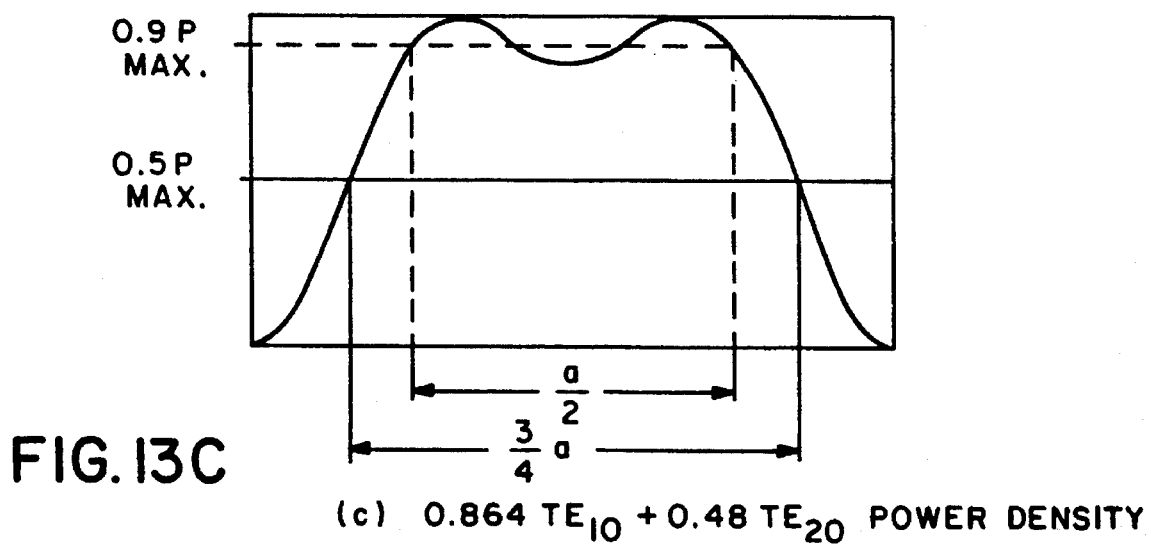

Details of a radio-frequency feed structure for the cavity resonator 202 may best be seen in FIGS. 12A, 12B and 12C. The cavity resonator 202 may in an alternative embodiment be fed from opposite sides by loop-type exciters 310 and 312. The loop exciter 310 is driven at a frequency of 40.68 megahertz while the loop exciter 312 is driven at twice that frequency, 81.36 megahertz. It may be appreciated that this arrangement allows a highly uniform average power to be present within the cavity. As may best be seen in FIG. 13A, a cavity having standing waves induced therein at the lowest mode, has an average power density with a peak at the center of the cavity. If the cavity is driven at a frequency of 81.36 megahertz a pair of power peaks occur, as may be seen in FIG. 13B. The continued effect of the two feeds of the twin feed cavity shown in FIGS. 12A through 12C is shown in FIG. 13C with the power density curve for a relative amplitude for power of 0.864 at the fundamental 40.68 megahertz frequency and a relative amplitude of 0.48 at the first octave or 81.36 megahertz frequency, thereby providing a highly uniform power across three quarters of the distance across the cavity as shown in FIG. 13C. This further provides uniform heating for the medical waste 16 within the cavity.

Referring now to FIGS. 3, 4, 5, 6 and 7, the gamma ray irradiating unit 50, which is of a type well known in the art, is shown therein. The gamma ray irradiation unit 50 includes a housing 500 comprised primarily of concrete, including an outer housing wall 502, a top housing wall 504 and interior walls 506 and 508. Walls 502 and 508 define an irradiation chamber 510 where the containers 17 containing the medical waste 16 may be irradiated. An input port 512, defined by a lower concrete wall 514 and a pair of concrete side walls 516 and 518, defines a trough-like region 520 through which a material handling apparatus 522 including a plurality of rails 524. A plurality of carts 526 may move on the plurality of rails 524. The material handling apparatus 522 extends through the tunnel 520 and around a bend 530 into a second tunnel 532 which allows the medical material 16 in the containers 17 to be quickly and easily transported in and out of substantially open tunnels to the gamma ray facility but which nevertheless, because of the zig-zag arrangement of the tunnels, prevents any escape of radiation to the environment. The source of radiation is contained in a source 540 containing a rack 542 holding cobalt 60 source rods 543 in total amounting to between one million and one and one-half million curies. The rack 542 is connected to a cable 544 coupled to a lifting apparatus 546 positioned on the outside of the wall 504. When it is desired to irradiate the containers 17, the lifting arrangement 546 lifts the source rack 542 and the accompanying cobalt 60 rods into the irradiation chamber 510. The source rack 542, while in the irradiation chamber 510, rests in a cage 556 positioned in the chamber 510 to prevent rods from accidentally falling into the irradiation chamber 510. Normally when the apparatus is not in use, the source 540 is stored in a well 560 filled with water below the irradiation chamber 510.

It may be appreciated that when the containers 17 are moved along the rails 522 to the irradiation chamber 510, there is handling equipment 570 within the irradiation chamber 510 which allows the containers 17 to be moved along a plurality of handling tracks 572 within the chamber 510 in such a way as that the containers 17 obtain substantially uniform exposure to the gamma ray flux within the irradiation chamber 510 from the source 540. The movement of the containers 17 on the carts 524 is timed in a well-known manner so that all containers obtain a substantially uniform dosage of gamma ray.

In the instant embodiment the containers are exposed to dosages of approximately 0.5 megarads which is sufficient to inactivate the bacteria and bacterial spores as well as any viruses not inactivated by the 60° heat from the radio-frequency treatment apparatus 48. Thus, the combination of the gamma ray flux and the heating of the medical materials substantially inactivates all of the microorganisms found thereon. The sharps are irradiated with a dosage of 1.5 megarads because they are not previously heated.

In an alternative the sharps may be compacted and mixed the aqueous foam and then heated to 60° C. in the radio frequency treatment apparatus. The sharps may then be irradiated with a dose of about 0.5 megarads to complete the disinfection process. After irradiation the disinfected sharps may be disposed of in a landfill or the like.

After the containers 17 are opened, the shredded disinfected general medical waste is placed in further containers containing a mixture of paper, plastic, and metal, which can be used as fuel. Possible users include cement kilns which burn fuel to create temperatures of about 130° C. or more and which might otherwise employ high sulfur coal. Because the general medical waste is low in sulfur, its use as fuel will not generate sulfur compounds which might be released into the atmosphere and contribute to acid rain.

It is believed that part of the superior effectiveness of the radio-frequency heating method disclosed herein is due to the fact that radio-frequency electromagnetic energy penetrates large boxes and volumetrically heats the contents thereof very efficiently. However, this factor alone is not believed to account entirely for the difference observed. It is further believed that the efficacious results of the instant process may be due to the fact that bacteria and viruses have a much higher water content than most of the mixed medical waste. As a result, the relatively high dielectric constant of the bacteria and viruses efficiently couples the electromagnetic or time-varying electromagnetic field energy to the water, causing rapid heating of the microorganisms and subsequent inactivation or destruction thereof. Substances with high dielectric constants selectively absorb radio-frequency energy. Therefore, radio-frequency energy may heat the bacteria and viruses to a lethal temperature before the surrounding waste reaches what is generally considered a lethal temperature.

The foregoing descriptions of the preferred embodiments of the present invention have been presented for purposes of illustration and description. They are not intended to be exhaustive or to limit the invention to the precise forms disclosed, and obviously many other modifications and variations are possible in light of the aforementioned teachings. The embodiments were chosen and described to best explain the principles of the invention and its practical applications, thereby enabling others skilled in the art to utilize best the invention in its various embodiments and with various modifications as are suited to the particular use contemplated.

What is claimed is:

1. A method of substantially uniformly disinfecting bulk heterogeneous medical waste comprising the steps of:

comminuting the bulk heterogeneous medical waste into comminuted bulk heterogeneous medical waste;

confining a quantity of the comminuted bulk heterogeneous medical waste comprising wet portions and dry portions in a closed treatment container;

exposing the treatment container to a time-varying electric field having a frequency less than the frequency of microwaves to evaporate water from the wet portions of the comminuted bulk heterogeneous medical waste, transporting the resulting water vapor by convection and diffusion to dry portions of the comminuted bulk heterogeneous medical waste, condensing some of said water vapor on cooler dry portions to wet the cooler portions, heating the wetted portions by the persisting time-varying electric field until all portions of the comminuted bulk heterogeneous medical waste are substantially uniformly heated by the time-varying electric field to provide substantially uniform disinfection throughout the comminuted bulk heterogeneous medical waste; and irradiating the treatment container with ionizing radiation.

2. A method of rendering heterogeneous medical material harmless according to claim 1, further comprising the step of comminuting the medical material into comminuted material.

3. A method of substantially uniformly disinfecting bulk heterogeneous medical waste according to claim 1, further comprising the step of heat soaking the heated comminuted bulk heterogeneous medical waste for a period of about 30 minutes.

4. A method of rendering heterogeneous medical material harmless according to claim 1, wherein the frequency of the radio-frequency electric field is less than the frequency of microwaves.

5. A method of substantially uniformly disinfecting bulk heterogeneous medical waste according to claim 1, wherein the ionizing radiation comprises gamma radiation.

6. A method of substantially uniformly disinfecting bulk heterogeneous medical waste according to claim 5, wherein the time-varying electric field has a frequency of about 500 kilohertz to about 600 megahertz.

7. A method of substantially uniformly disinfecting bulk heterogeneous medical waste according to claim 5, wherein the gamma radiation is produced by cobalt 60.

8. A method of substantiality uniformly disinfecting bulk heterogeneous medical waste according to claim 5, wherein the gamma radiation is produced by cesium 137.

9. A method of substantially uniformly disinfecting bulk heterogeneous medical waste according to claim 1, further comprising the step of adding water to the comminuted bulk heterogeneous medical waste.

10. A method of substantially uniformly disinfecting bulk heterogeneous medical waste according to claim 9, wherein the step of adding water further comprises adding to the comminuted bulk heterogeneous medical waste a foam comprising a mixture of water and a surfactant.

11. A method of substantially uniformly disinfecting bulk heterogeneous medical waste according to claim 9, further comprising the step of compacting the comminuted bulk heterogeneous medical waste.

12. Apparatus for substantially uniformly disinfecting bulk heterogeneous medical waste comprising:

comminuter for comminuting the bulk heterogeneous medical waste into comminuted bulk heterogeneous medical waste a radio-frequency treatment unit for accepting the comminuted bulk heterogeneous medical to be disinfected;

means for transporting comminuted bulk heterogeneous medical waste in substantially closed bulk containers through the radio-frequency treatment unit; and means for energizing the radio-frequency treatment unit with a time-varying electric field having a frequency below the frequency of microwaves to substantially uniformly heat wetted portions of the comminuted bulk heterogeneous medical waste to provide substantially uniform disinfection throughout the comminuted bulk heterogeneous medical waste; and means for irradiating the comminuted bulk heterogeneous medical waste with ionizing radiation.

13. Apparatus for substantially uniformly disinfecting bulk heterogeneous medical according to claim 12, further comprising means for soak heating the comminuted bulk heterogeneous medical waste after it exits the radio-frequency treatment unit.

14. An apparatus for treating infectious medical material according to claim 12, further comprising means for rotating the medical material with respect to the time-varying electric field to provide more uniform exposure of the medical material to the time-varying electric field.

15. An apparatus for treating medical material according to claim 12, further comprising means for injecting inert gas into the radio-frequency treatment unit to sweep oxygen therefrom to avoid oxidizing heated medical material and to cause a flow of gas from a relatively cool portion of the radio-frequency treatment unit to a relatively warm portion to prevent any vapor which might have escaped from the medical material from condensing on cooler medical material entering the radio-frequency treatment unit.

16. Apparatus for substantially uniformly disinfecting bulk heterogeneous medical waste according to claim 12, wherein said means for irradiating further comprises a source of gamma radiation.

17. Apparatus for substantially uniformly disinfecting bulk heterogeneous medical waste according to claim 16, wherein said source of gamma radiation comprises cobalt 60.

18. An apparatus for treating medical material according to claim 12, further comprising means for comminuting the medical material.

19. Apparatus for substantially uniformly disinfecting bulk heterogeneous medical waste according to claim 12, further comprising means for compacting the comminuted bulk heterogeneous medical waste.

* * * * *

UNITED STATES PATENT AND TRADEMARK OFFICE
CERTIFICATE OF CORRECTION

PATENT NO. : 5,523,052
DATED : June 4, 1996
INVENTOR(S) : Bridges, et al.

It is certified that error appears in the above-indentified patent and that said Letters Patent is hereby corrected as shown below:

Column 24, cancel lines 33-36.

Column 24, cancel lines 42-45.

Column 25, line 9, after "waste" insert --;-- (semicolon).

Column 25, line 11, after "medical" insert --waste--.

Column 25, line 26, after "medical" insert --waste--.

Column 25, cancel lines 30 and 31.

Column 26, cancel lines 1-13.

Column 26, cancel lines 23-25.

Signed and Sealed this

Eleventh Day of February, 1997

Attest:

BRUCE LEHMAN

*Attesting Officer*  *Commissioner of Patents and Trademarks*